(12) United States Patent
Wang et al.

(10) Patent No.: US 11,808,051 B2
(45) Date of Patent: Nov. 7, 2023

(54) PORTABLE, MODULAR, MULTI-PURPOSE ENCLOSURE

(71) Applicants: Anthony Wang, Brooklyn, NY (US); Nathan Weinstein, Pelham, NY (US); David Haft, Pelham, NY (US)

(72) Inventors: Anthony Wang, Brooklyn, NY (US); Nathan Weinstein, Pelham, NY (US); David Haft, Pelham, NY (US)

( * ) Notice: Subject to any disclaimer, the term of this patent is extended or adjusted under 35 U.S.C. 154(b) by 230 days.

(21) Appl. No.: 17/234,579

(22) Filed: Apr. 19, 2021

(65) Prior Publication Data

US 2021/0324645 A1 Oct. 21, 2021

Related U.S. Application Data

(60) Provisional application No. 63/012,774, filed on Apr. 20, 2020.

(51) Int. Cl.
| | |
|---|---|
| *E04H 1/12* | (2006.01) |
| *A61L 2/10* | (2006.01) |
| *A47K 11/02* | (2006.01) |
| *A47K 3/28* | (2006.01) |

(52) U.S. Cl.
CPC ............ *E04H 1/1216* (2013.01); *A61L 2/10* (2013.01); *E04H 1/1244* (2013.01); *A47K 3/28* (2013.01); *A47K 11/02* (2013.01); *A61L 2202/11* (2013.01); *A61L 2202/16* (2013.01)

(58) Field of Classification Search
CPC ... E04H 1/1216; E04H 1/1205; E04H 1/1211; E04H 1/1222; E04H 1/1227; E04H 1/1223; E04H 1/1238; E04H 1/1244; E04H 1/1277; E04H 1/1266; E04H 2001/1294; E04H 9/14; E04H 9/145; E04H 15/001; E04H 15/003; E04H 15/008; E04H 15/24; A47K 11/02; A47K 11/04; A47K 3/325; A47K 3/328; A61L 2/10; A61L 2202/11; A61L 2202/16
See application file for complete search history.

(56) References Cited

U.S. PATENT DOCUMENTS

| | | | |
|---|---|---|---|
| 4,031,572 A * | 6/1977 | Harding | A47K 11/02 D25/16 |
| 4,380,836 A | 4/1983 | Braxton | |
| (Continued) | | | |

FOREIGN PATENT DOCUMENTS

| | | | | |
|---|---|---|---|---|
| EP | 3048217 A2 * | 7/2016 | ........... | E04H 1/1205 |
| FR | 2725227 A1 * | 4/1996 | ........... | E04H 1/1205 |
| (Continued) | | | | |

*Primary Examiner* — Kyle J. Walraed-Sullivan
(74) *Attorney, Agent, or Firm* — Lowenstein Sandler LLP

(57) ABSTRACT

A portable enclosure includes a bottom component including a first sidewall that forms a first door opening. The portable enclosure further includes a top component including a second sidewall that forms a second door opening. The top component is configured to removably attach to the bottom component to align the first door opening and the second door opening and to at least partially enclose an interior volume of the portable enclosure. The portable enclosure further includes a door configured to removably attach to the top component and the bottom component to cover the first door opening and the second door opening.

20 Claims, 18 Drawing Sheets

(56) References Cited

U.S. PATENT DOCUMENTS

| | | | |
|---|---|---|---|
| 4,974,265 A * | 12/1990 | Maggio | A47K 3/325 |
| | | | 135/901 |
| 4,979,242 A | 12/1990 | Maggio | |
| 5,544,369 A | 8/1996 | Roberts | |
| 6,434,896 B1 * | 8/2002 | Mitchell | E04H 9/14 |
| | | | 52/80.2 |
| D519,645 S * | 4/2006 | Wright | D25/16 |
| 7,185,375 B1 | 3/2007 | Movsas | |
| 7,200,878 B2 | 4/2007 | Payne | |
| 7,313,833 B2 | 1/2008 | Wee | |
| 7,540,041 B2 | 6/2009 | Gara | |
| 7,992,739 B2 | 8/2011 | Garcia | |
| 8,256,443 B2 * | 9/2012 | Neal | E04H 1/1244 |
| | | | 135/96 |
| 8,499,371 B1 | 8/2013 | Becker | |
| 8,998,246 B2 | 4/2015 | Griffard | |
| 9,097,032 B1 * | 8/2015 | Al-Saffar | E04H 9/16 |
| 9,260,876 B1 | 2/2016 | Brown | |
| 9,289,101 B2 | 3/2016 | Weir | |
| 9,518,398 B2 * | 12/2016 | Taylor | E04H 1/1216 |
| 9,765,542 B1 * | 9/2017 | Broughton | E04H 1/1216 |
| 9,993,123 B2 | 6/2018 | Moise | |
| 2003/0024191 A1 * | 2/2003 | Hampel | E04H 1/1216 |
| | | | 52/309.1 |
| 2003/0208838 A1 * | 11/2003 | Mason | E04H 1/1216 |
| | | | 4/449 |
| 2004/0216395 A1 * | 11/2004 | Wentworth, Jr. | B60P 3/34 |
| | | | 52/79.5 |
| 2008/0209624 A1 * | 9/2008 | Lavoie | E04H 1/1216 |
| | | | 4/144.1 |
| 2013/0055499 A1 | 3/2013 | Miguel Serda | |
| 2016/0160516 A1 * | 6/2016 | Brown | A47K 11/12 |
| | | | 4/476 |
| 2019/0063090 A1 * | 2/2019 | Schimmel | A47K 3/325 |
| 2019/0142231 A1 * | 5/2019 | Nelson | A47K 11/026 |
| | | | 4/483 |
| 2020/0147248 A1 * | 5/2020 | Mintie | A61L 2/10 |
| 2021/0330844 A1 * | 10/2021 | Holden | A61L 2/26 |

FOREIGN PATENT DOCUMENTS

| | | | | |
|---|---|---|---|---|
| GB | 2504664 A | * | 2/2014 | E04H 1/1205 |
| WO | WO-2012145933 A1 | * | 11/2012 | A61H 33/06 |

* cited by examiner

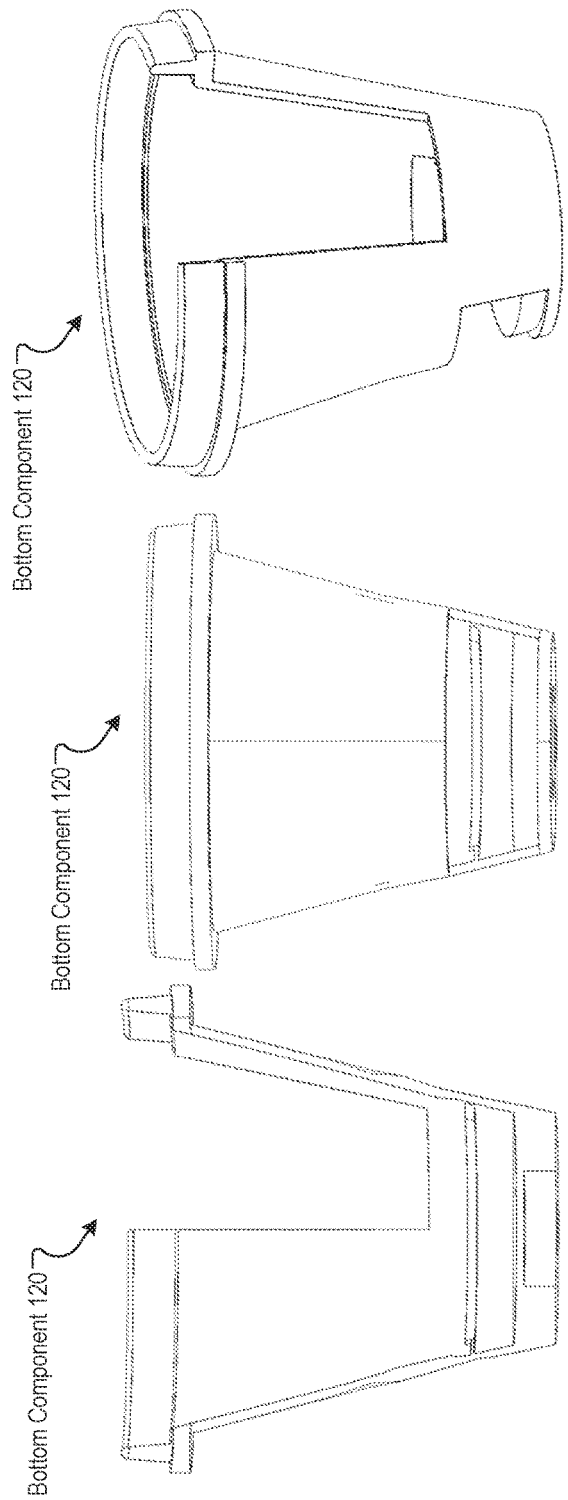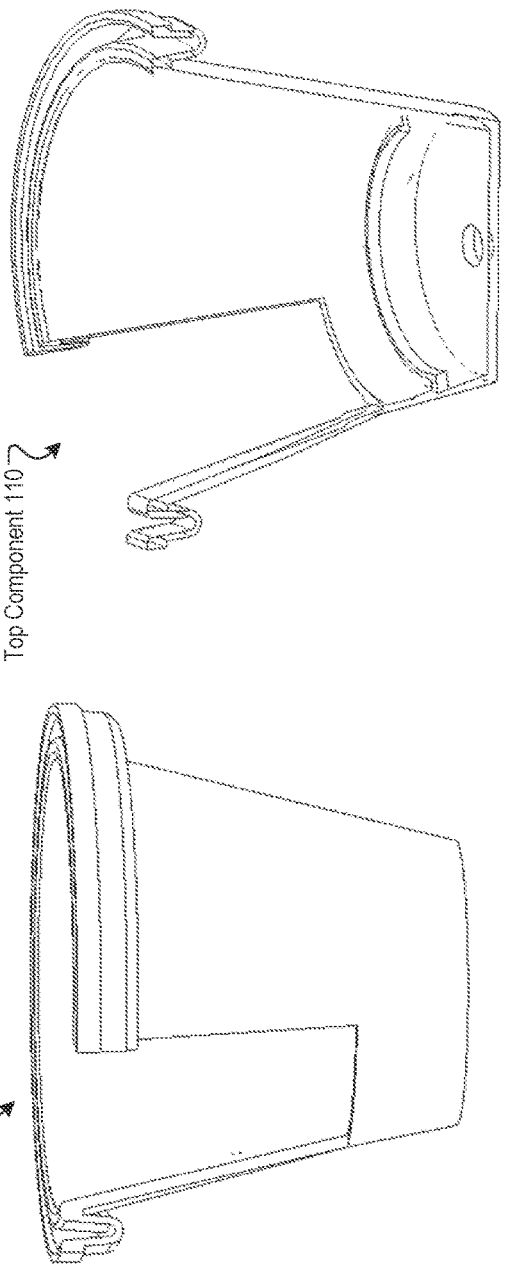

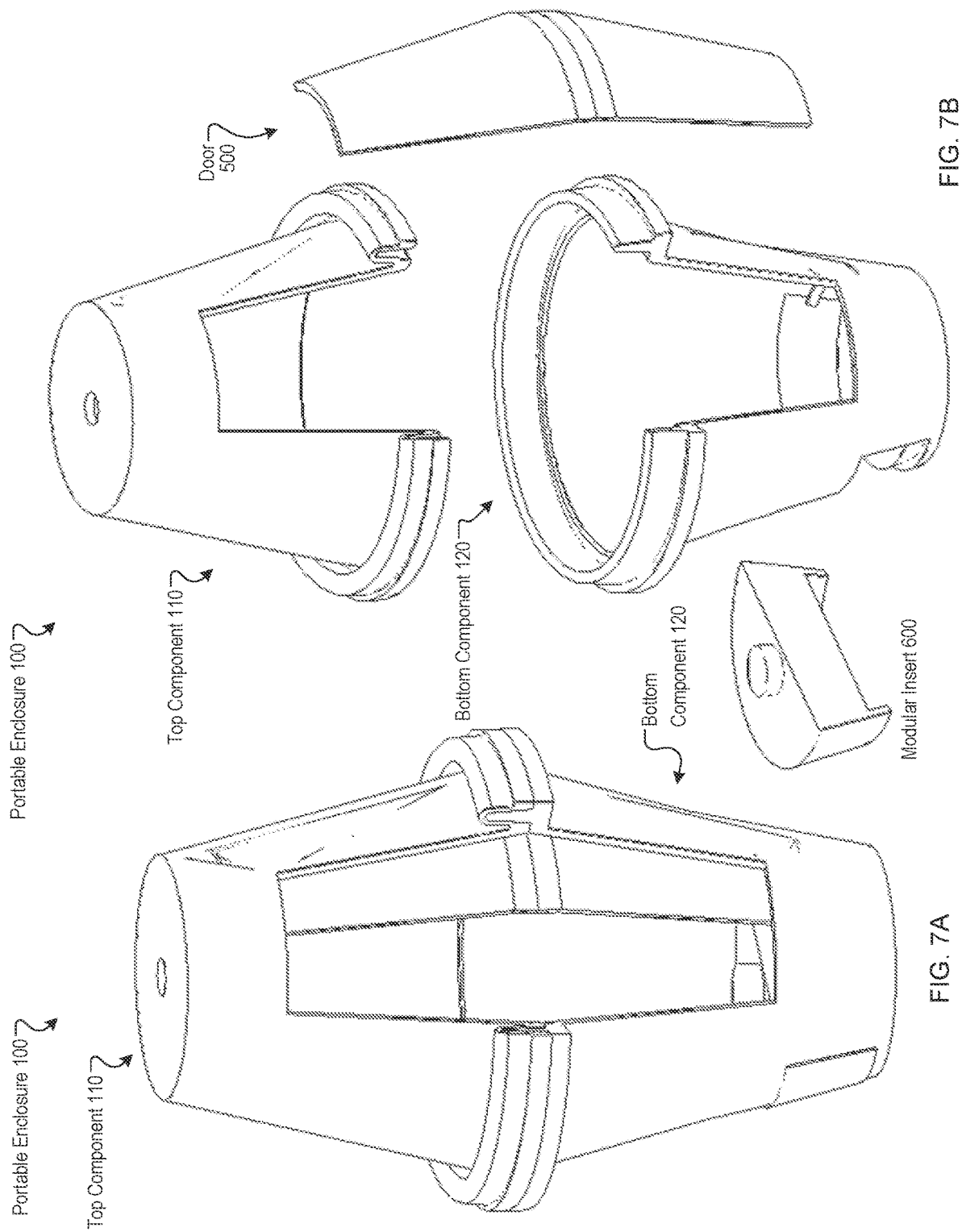

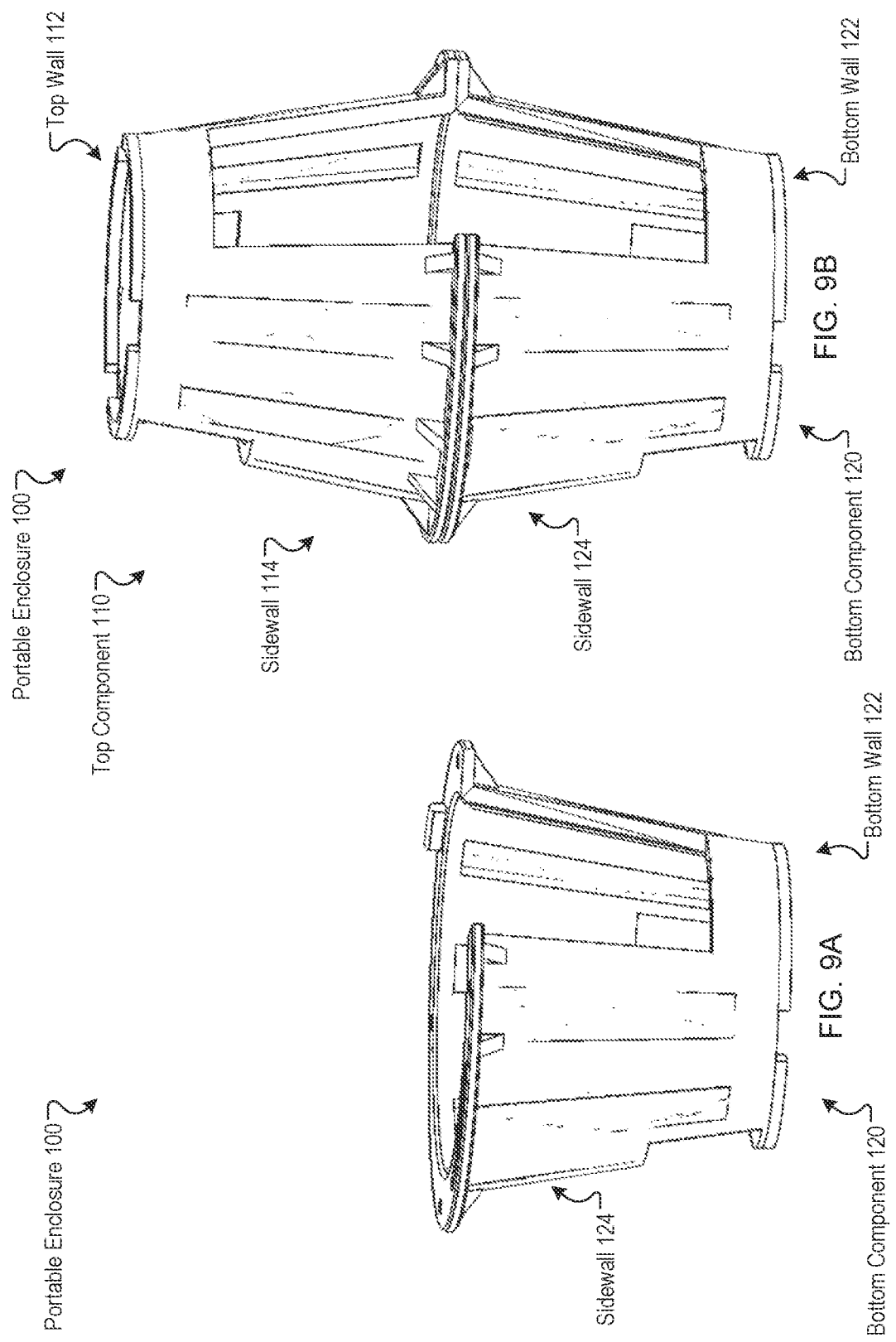

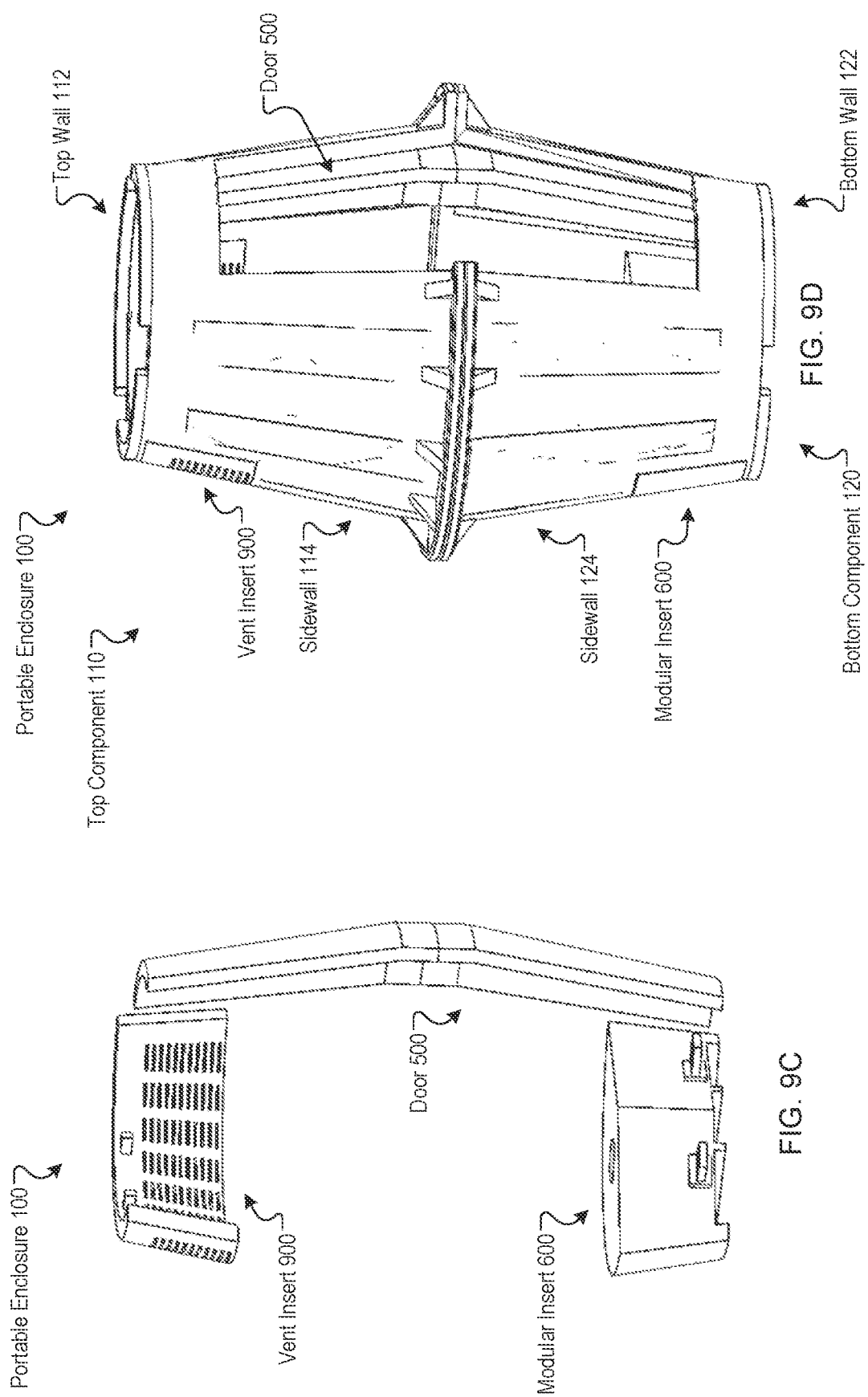

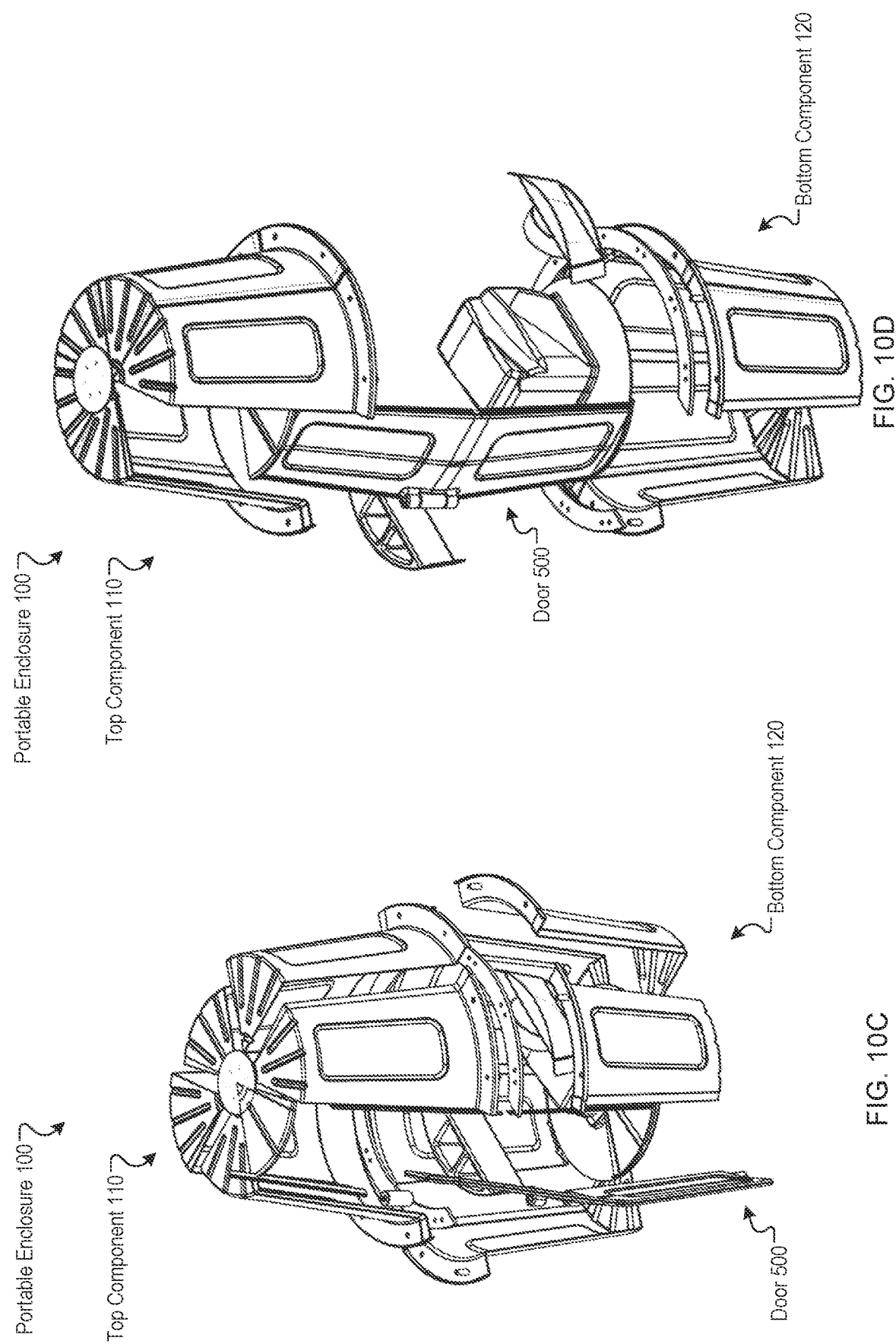

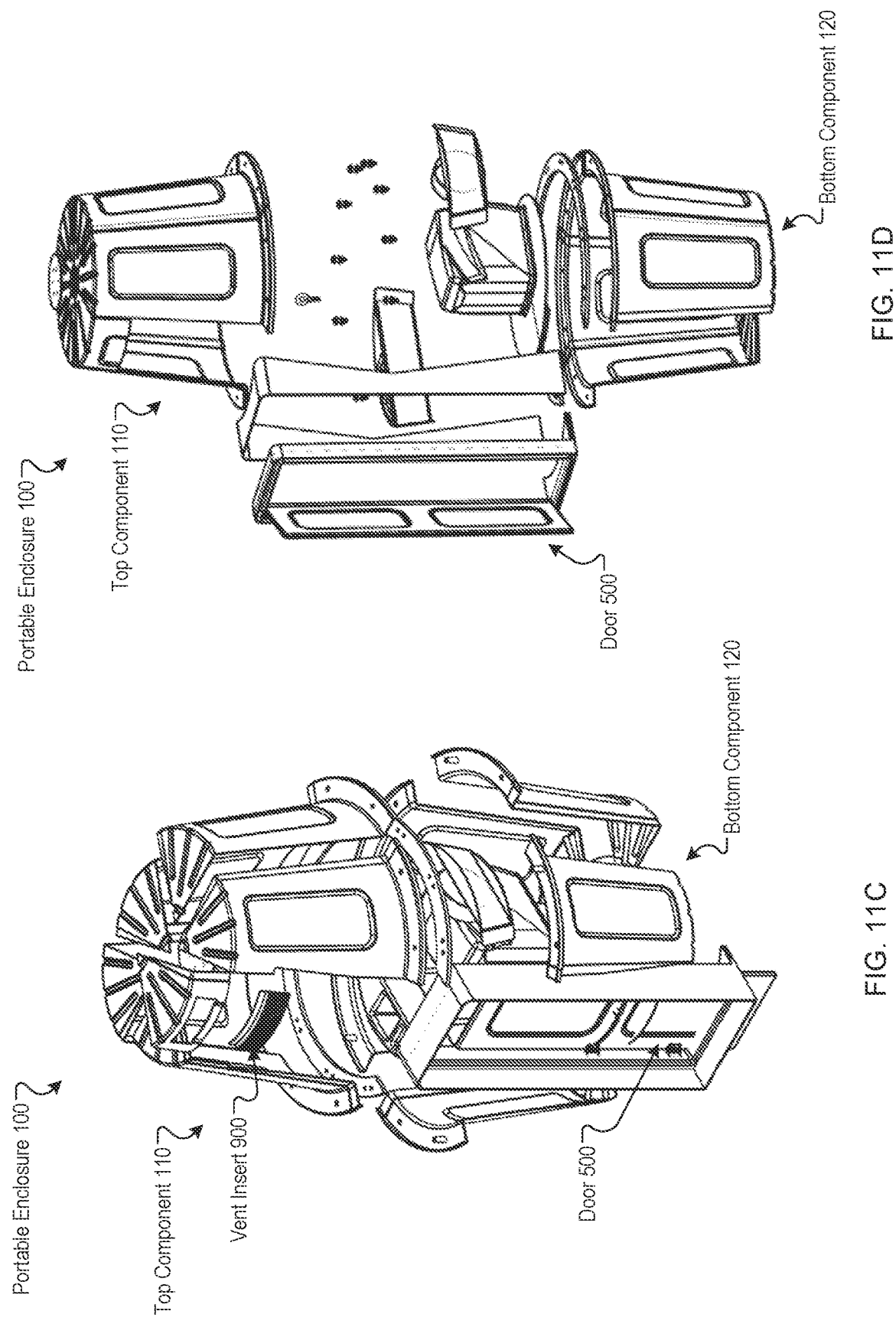

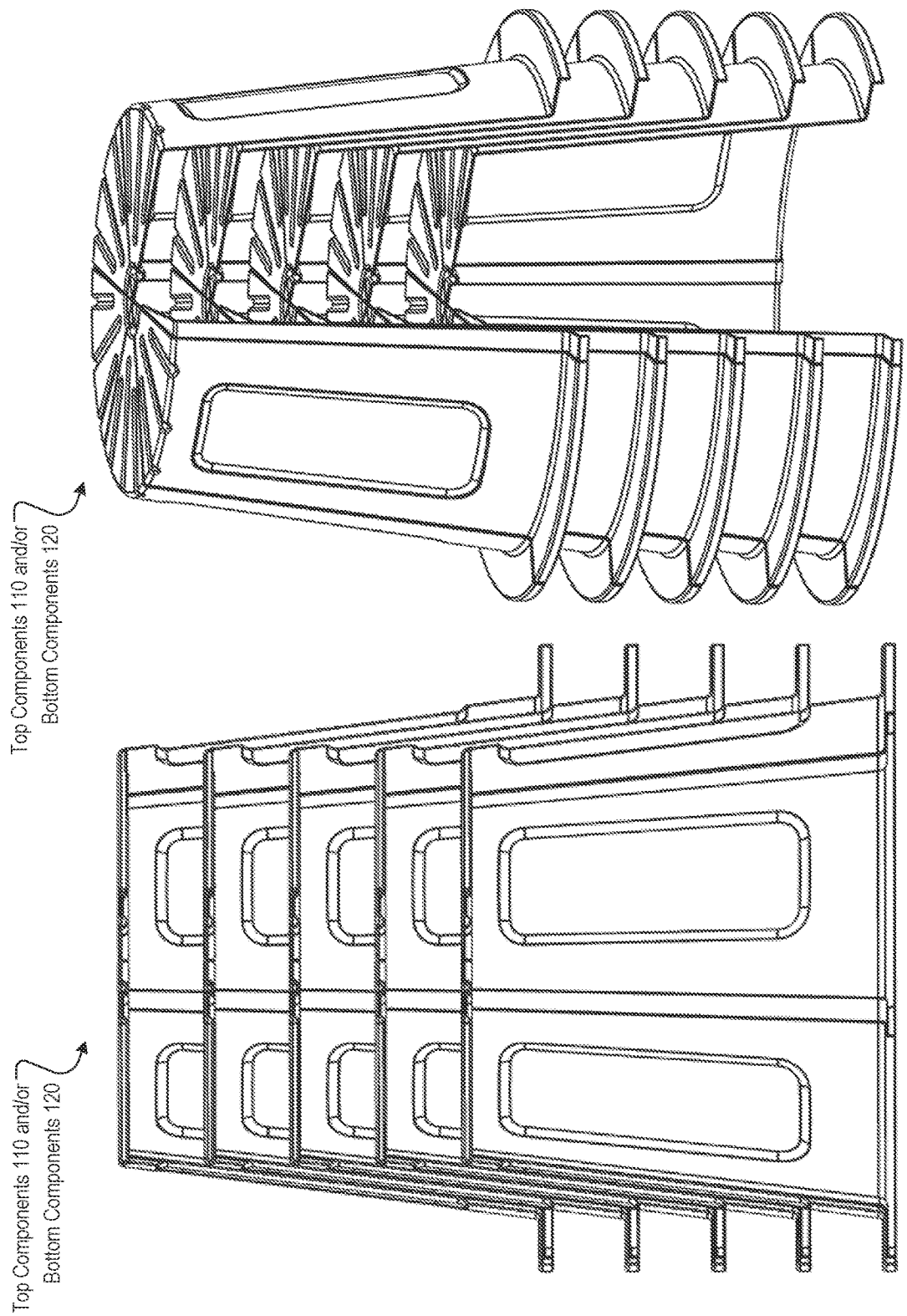

PORTABLE, MODULAR, MULTI-PURPOSE ENCLOSURE

RELATED APPLICATION

This application claims benefit of U.S. Provisional Patent Application 63/012,774, filed Apr. 20, 2020, the entire content of which is incorporated by reference herein.

BACKGROUND

Enclosures are provided in remote locations such as construction sites, festivals, camping sites, etc. In some examples, an enclosure houses a toilet.

BRIEF DESCRIPTION OF DRAWINGS

The examples described herein will be understood more fully from the detailed description given below and from the accompanying drawings, which, however, should not be taken to limit the application to the specific examples, but are for explanation and understanding only.

FIGS. 3A-C illustrate views of a bottom component of a portable enclosure, according to certain embodiments.

FIGS. 4A-B illustrate views of a top component of a portable enclosure, according to certain embodiments.

FIGS. 7A-C illustrate perspective views of a portable enclosure, according to certain embodiments.

FIGS. 9A-D illustrate components of portable enclosures, according to certain embodiments.

FIGS. 10A-D illustrate views of portable enclosures, according to certain embodiments.

FIGS. 11A-D illustrate views of portable enclosures, according to certain embodiments.

FIGS. 15A-B illustrate stacked components of portable enclosures, according to certain embodiments.

DETAILED DESCRIPTION

Figures 1A, 1B:
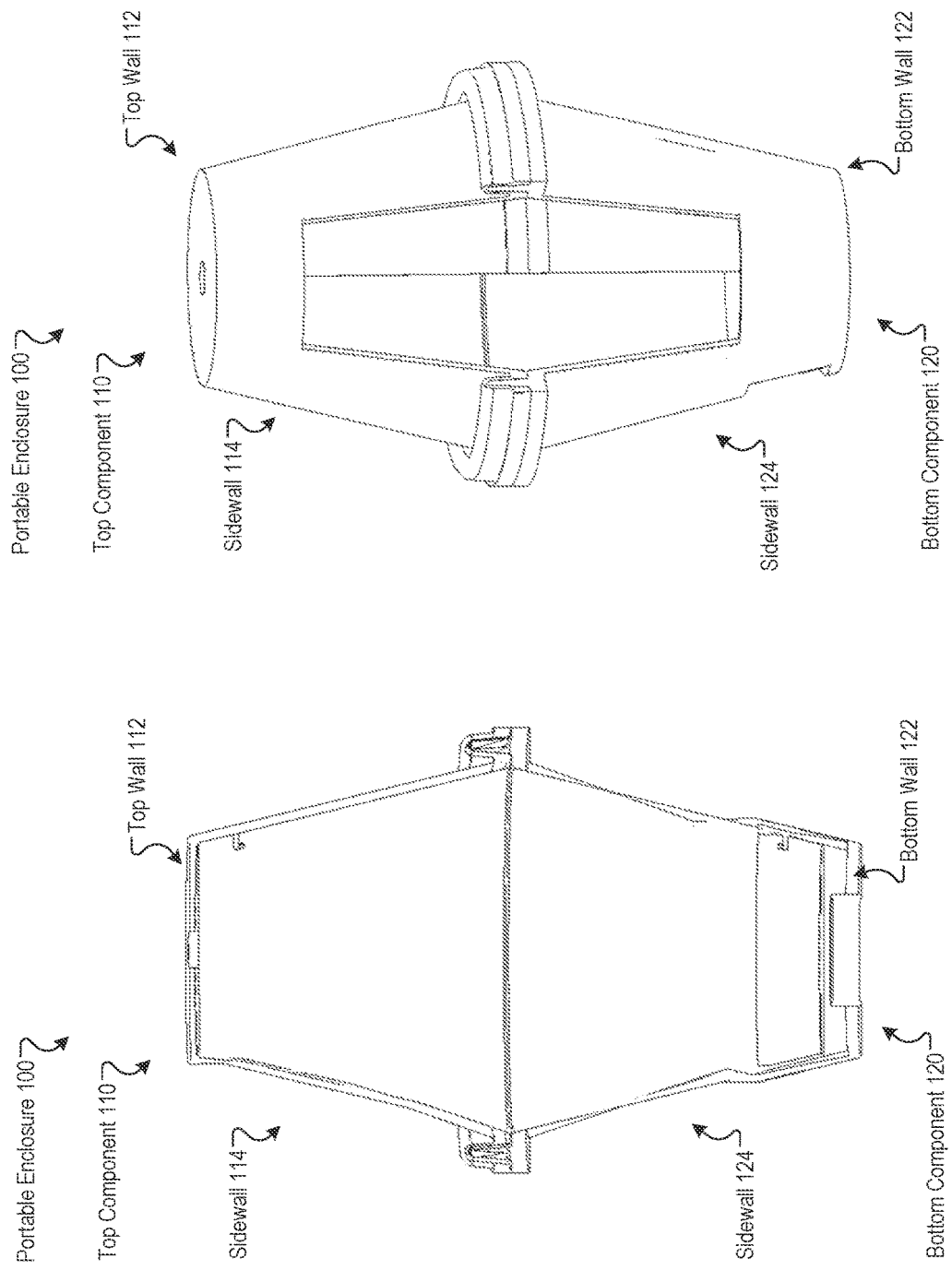
FIGS. 1A-B illustrate views of a portable enclosure in an assembled configuration, according to certain embodiments.

Embodiments described herein are related to a portable, modular, multi-purpose enclosure.

Enclosures provide privacy for a user. In some examples, an enclosure houses a toilet (e.g., the enclosure is a porta potty). Conventional enclosures, such as porta potties, are lifted and transported by heavy lifting equipment. Some conventional enclosures are to remain in an upright position when being transported to a location for usage and/or when being transported from the location where used. Conventional enclosures occupy a large surface area and height clearance in transportation and storage. Some conventional enclosures are unsanitary (e.g., do not provide proper ways for a user to clean their hands after usage of the enclosure).

The devices, systems, and methods disclosed herein provide a portable modular, multi-purpose enclosure (e.g., a portable enclosure). A portable enclosure includes a bottom component, a top component, and a door. In some embodiments, the bottom component is stackable with at least one of one or more bottom components of other portable enclosures and/or one or more top components. In some embodiments, the top component is stackable with at least one of one or more top components of other portable enclosures and/or one or more bottom components. In some embodiments, the portable enclosure includes a modular insert and the modular insert is stackable with one or more modular inserts of other portable enclosures. In some embodiments, the door is stackable with one or more doors of other portable enclosures.

In some embodiments, the bottom component has a truncated conical shape (e.g., a hollow conical frustum, a truncated hollow right circular cone, a cup shape, etc.). The bottom component includes a bottom wall and one or more sidewalls (e.g., a single sidewall, a conical sidewall, a sidewall that has a circular perimeter, etc.) that have a first distal end attached to (e.g., integral to) the bottom wall and a second distal end that forms an interconnecting feature. The one or more sidewalls of the bottom component form a first door opening configured to receive a first portion of the door and an insert opening configured to receive the modular insert.

In some embodiments, the top component has a truncated conical shape (e.g., a hollow conical frustum, a truncated hollow right circular cone, cup shape, etc.). In some embodiments, the top component is substantially the same shape (e.g., substantially the same dimensions) as the bottom component (e.g., the top component and the bottom component are substantially equal halves). The top component includes a top wall and one or more sidewalls (e.g., a single sidewall, a conical sidewall, a sidewall that has a circular perimeter, etc.) that have a first distal end attached to the top wall and a second distal end that forms an interconnecting feature configured to removably attach to the interconnecting feature of the bottom component. The one or more sidewalls of the top component form a second door opening configured to receive a second portion of the door. Responsive to the top component being attached to the bottom component, the top component and the bottom component at least partially enclose an inner volume.

The first door opening and the second door opening are aligned responsive to the top component being attached to the bottom component. The door is configured to removably attach to the top component and the bottom component to cover (e.g., slidably cover, swing to cover) the first door opening and the second door opening.

In some embodiments, the modular insert removably inserts into the bottom component via an insert opening formed by the bottom component. In some embodiments, the portable enclosure is a portable toilet structure (e.g., the modular insert includes or is used in conjunction with a toilet). In some embodiments, the portable enclosure is a portable shower structure (e.g., the modular insert includes water to be supplied to or waste received from the shower structure). In some embodiments, the portable enclosure is a portable changing room structure.

In some embodiments, the bottom component and/or the top component are made from panels. In some examples, a plurality of panels (e.g., five panels) connect to each other to form the bottom component or the top component. Each panel may have a top wall that is substantially horizontal, a bottom wall that is substantially horizontal, and a sidewall disposed between the top wall and the bottom wall. The top wall of a panel may be a sector (e.g., circular sector, shape of a pizza slice, etc.). The bottom all of the panel may have a perimeter that is an inner arc and an outer arc. The sidewall may be angled to form an angle between the bottom surface of the top wall and an interior surface of the sidewall that is greater than ninety degrees. Each panel may include a front flange extending along the top wall, the sidewall, and the bottom wall. Each panel may include a rear feature extending along the top wall, the sidewall, and the bottom wall. The rear feature may be opposite the front flange. The front flange may be configured to couple to a corresponding rear feature of another panel. The rear feature may be configured to couple to a corresponding front flange of another panel. The bottom wall may be configured to be attached to a bottom wall of another panel.

Aspects of the present disclosure have advantages over conventional solutions. The portable enclosure of the present disclosure is modular and stackable to occupy less room (e.g., less surface area, less height clearance) for transportation and storage compared to conventional solutions. The portable enclosure may have components (e.g., a modular insert, toilet, urinal, toilet paper holder, etc.) that can be removed from the enclosure during transport and storage, thus allowing the top component and the bottom component to be transported and/or stored in different positions (e.g., upside down, sideways, upright, etc.) compared to conventional solutions. In some embodiments, the components of the portable enclosure can be lifted and/or transported without heavy lifting equipment due to being modular (e.g., removably attachable to each other). The portable enclosure is modular and allows for modular addition of components to maintain sanitation of the portable enclosure and the users (e.g., components to provide proper ways for a user to clean their hands after usage of the enclosure). The top component and the bottom component may be made of panels which may provide increased ease of manufacturing instead of manufacturing one large component.

FIGS. 1A-B illustrate views of a portable enclosure 100 in an assembled configuration, according to certain embodiments. FIG. 1A is a cross-sectional front view of the portable enclosure 100 in an assembled configuration. FIG. 1B is a perspective view of the portable enclosure in an assembled configuration. In some embodiments, FIGS. 1A-B illustrate a top and bottom halves (e.g., top component 110 and bottom component 120) assembled with cross section indicating the male and female connector allowing fast and easy mating of the two components.

Figure 2A:
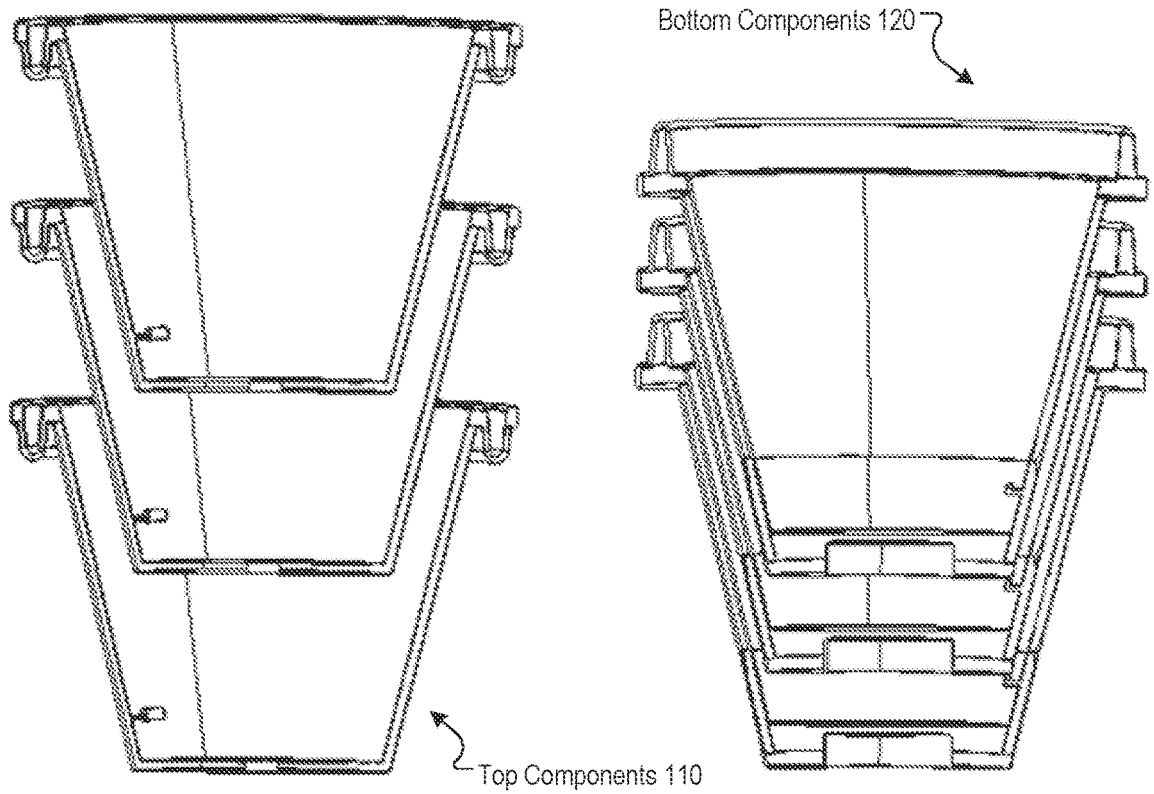
FIGS. 2A-B illustrate views of stacked components of a portable enclosure, according to certain embodiments.
Figure 2B:
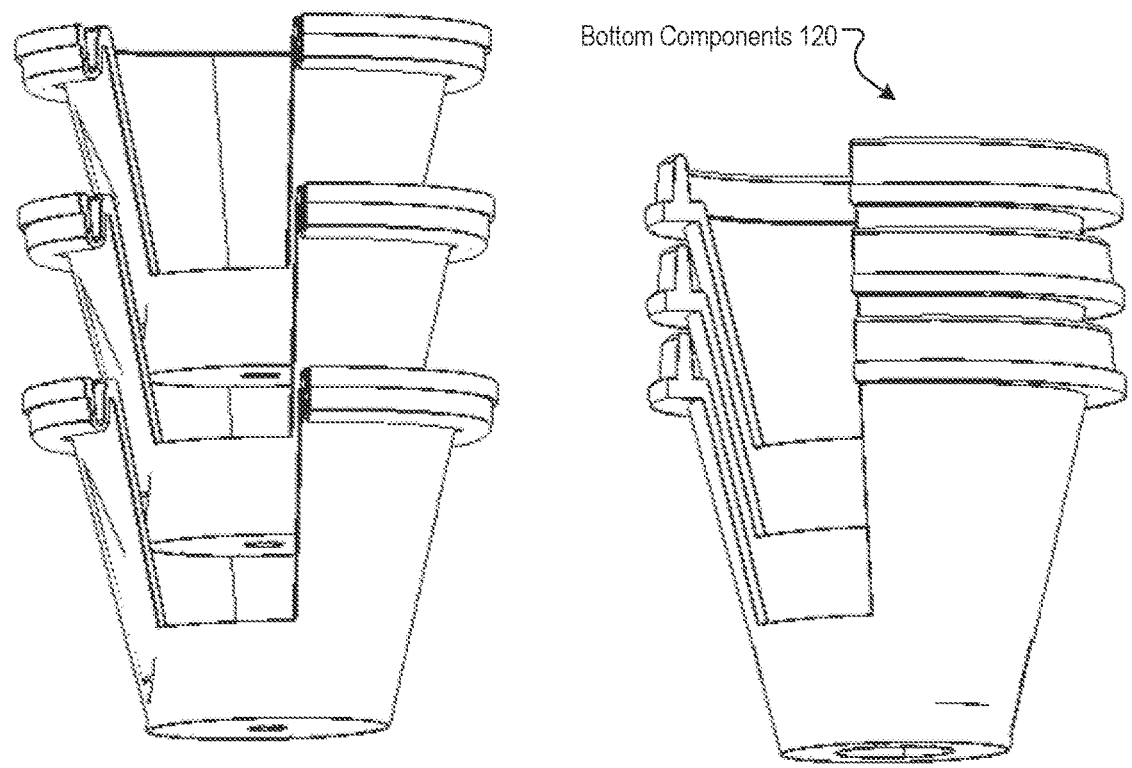

FIGS. 2A-B illustrate views of stacked components (e.g., top component 110 and/or bottom component 120) of a portable enclosure 100, according to certain embodiments. FIG. 2A is a cross-sectional front view of the stacked components (e.g., top component 110 and/or bottom component 120) of the portable enclosure 100. FIG. 2B is a perspective view of the stacked components (e.g., top component 110 and/or bottom component 120) of the portable enclosure 100. FIGS. 2A-B illustrate the bottom and top halves (e.g., top component 110 and bottom component 120) stacked for space reduction during storage and transportation.

FIGS. 3A-C illustrate views of a bottom components 120 of a portable enclosure 100, according to certain embodiments. FIG. 3A is a cross-sectional rear view of the bottom component 120. FIG. 3B is a rear view of the bottom component 120. FIG. 3C is a perspective view of the bottom component 120. FIGS. 3A-C illustrate the bottom component 120 that includes a track that accommodates the sliding door, an opening that becomes a part of the door frame, and an aperture for a modular insert to enter through. In some embodiments, the bottom component 120 forms an opening at the bottom wall for fixture to the base plate.

FIGS. 4A-B illustrate views of a top component 110 of a portable enclosure 100, according to certain embodiments. FIG. 4A is a perspective view of the top component 110. FIG. 4B is a perspective view of the top component 110. In some embodiments, the top component 110 includes one or more of a female connector to join with the bottom component, an opening at the top (e.g., for ventilation, lighting, and/or other additional components), a track for hosting the sliding door, and opening for the door frame, and a tapered outer design.

In some embodiments, the portable enclosure 100 is a portable, modular, multi-purpose enclosure. In some embodiments, the portable enclosure 100 is a portable, modular toilet enclosure. The portable enclosure 100 has multiple structural components including a top-portion (e.g., top component 110) that connects to a bottom-portion (e.g., bottom component 120), a sliding insert (e.g., modular insert) for extended functionality, and a door. When assembled, the portable enclosure 100 serves as an enclosure which provides privacy to the occupant. When disassembled, components (e.g., top component 110 and/or bottom component 120) of portable enclosures 100 stack on top of each other for improved space efficiency, easy transport, and reduced storage space.

The top component 110 is removable. The top component 110 in the affixed position (e.g., assembled configuration) fits onto the bottom component 120 and is secured to the bottom component 120 through a specifically designed junction. The junction, female and male on either end allows the two halves to be easily mated and assembled. In the affixed position, the top component 110 and the bottom component 120 form a structure (e.g., portable enclosure 100), the interior space (e.g., interior volume) of which is hollow and can serve as a portable toilet enclosure, as a portable shower enclosure, as a changing room, as a storage unit, and/or as a private area that separates the user from outer space. The bottom component 120 and the top component 110 have matching cut-outs (e.g., first door opening and second door opening) which in the affixed position work in conjunction to form a door-frame. In some embodiments, the door frame hosts a sliding door which in the closed position completes the structure, providing privacy to the occupant. The door frame can slide open to allow entry and exit of the user from the structure. The sliding door mechanism is specifically designed so the operator can simply insert the sliding door into the track located in the top and bottom component to accommodate the door without any additional hinges, screws, or any sort of fastener. The door can then be secured to the main frame of the unit to form a lock that is only accessible by the user from within the unit. When the door is slid shut and the lock is engaged from the inside, a small exterior panel indicates that the unit is occupied. In some embodiments, the door is a hinged door and a similar lock/indicator panel component exists.

Figure 6A:
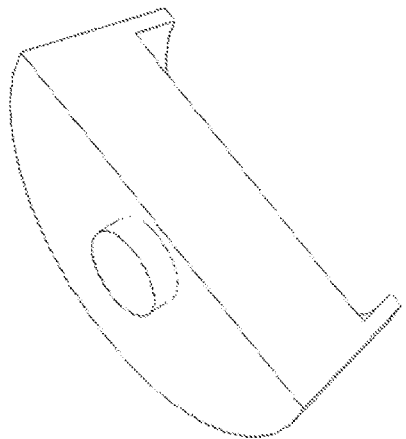
FIGS. 6A-B illustrate views of a modular insert of a portable enclosure, according to certain embodiments.
Figure 6B:
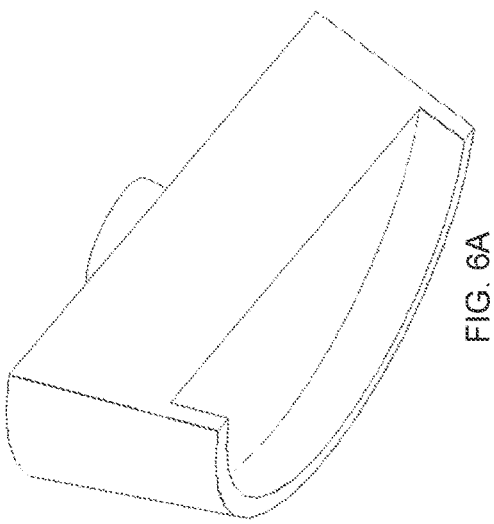

FIGS. 6A-B illustrate views of a modular insert 600 of a portable enclosure 100, according to certain embodiments. FIG. 6A illustrates a bottom perspective view. FIG. 6B illustrates a top perspective view.

In some embodiments, the modular insert 600 slides into the aperture of the bottom component. In some embodiments, the modular insert 600 functions as a cesspool to contain chemicals for dissolving liquid and solid waste from users. In some embodiments, the top opening serves as a connector to extended toilet seating for the convenience of the user. In some embodiments, the insert serves as a water tank to hold water and includes a pumping mechanism (e.g., pumping device, pumping component, pump, etc.). Water is then dispensed through a series of piping that connects to an opening such as a shower head.

The bottom component 120 forms another, separate aperture (e.g., insert opening) into which additional functional components can selectively be placed. In some embodiments, modular insert 600 including a cesspool or waste tank is inserted into the aperture therein affixing within the unit, as a waste collection module for human waste and other solid and liquid waste. The modular waste-tank in some embodiments is complete in-and-of itself, serving as both a waste tank, and having a top-shape which forms a toilet seat and or seat and cover. In some embodiments, the waste tank goes in through the aperture as described, and then an additional toilet module is brought in through the door opening (e.g., and or from above before the top component is attached to the bottom component) and placed on top of the tank, where it sits or is affixed. In some embodiments the waste tank slides into the aperture as described, and then has additional accordion capability once in-place within the structure, to form a seat that rises up to a higher profile. In some embodiments, a water tank is inserted into the aperture (e.g., insert opening in the bottom component), with a pipe, hose, or tubing reaching up to the top of the unit, then curling back down slightly, to form a shower head, to turn the enclosure into a functional shower. In some embodiments a power unit or power pack is placed into the aperture, allowing the occupant to have both privacy and access to electrical power. In some embodiments, other equipment is slid into the aperture, including communications equipment, a chemical tank, or a cushioning material. Additionally, a wall-shaped modular component can affix to the aperture, and thereafter seal-off the aperture while providing privacy to an occupant in the enclosure, without additional functionality, and as a place-holder between using other modular components. In some embodiments the aperture hosts a drain module that draws away water or waste. In some embodiments the drain module co-functions with the shower unit, or the waste unit, to extend functionality beyond the enclosure, such as the ability to drain water or waste.

In some embodiments (e.g., all instances of being affixed), the components of the portable enclosure are able to fit together by design and once the top component 110 is affixed to the bottom component 120 of the portable enclosure, the top component 110 rests with stability on the bottom component 120. In some embodiments, the top component 110 is affixed to the bottom component 120 with a clamp mechanism (e.g., clamping device, clamp component, etc.). This clamp mechanism has a small aperture, or multiple small apertures through which one or more locks (e.g., a small lock or locks) can be placed to maintain the efficacy of the clamp. In some embodiments the top component 110 clicks into the bottom component using a plastic mechanism or multiple plastic mechanisms which slide in easily from top-to-bottom, but which provide the inability to slide-up without being pushed in laterally simultaneously. In some embodiments, the top component 110 affixes to the bottom component 120 and then is rotated several degrees so that the flange of the bottom component 120 covers the flange of the top component making the top component 110 irremovable from the bottom component 120 without re-sliding in the opposite direction. In all instances the ability to utilize a lock, such as a padlock, in conjunction with the clamp, click, or flange mechanism for security and stability is an option, at least in one or multiple embodiments. In some embodiments the locking mechanism (e.g., locking device, locking component) is built-in to the clamp, click, and/or flange mechanism and is part of the portable enclosure.

Figure 5A:
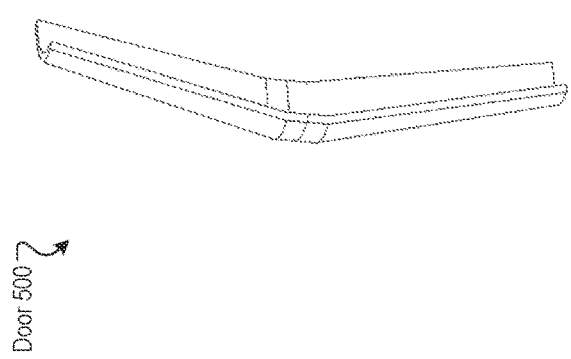
FIGS. 5A-B illustrate views of a door of a portable enclosure, according to certain embodiments.
Figure 5B:
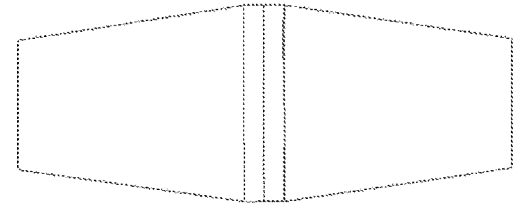

FIGS. 5A-B illustrate views of a door 500 of a portable enclosure 100, according to certain embodiments. FIG. 5A illustrates a front view of the door 500. FIG. 5B illustrates a side view of the door 500. In some embodiments, the door 500 (e.g., sliding door) fits the curvature of the tracks in the top component 110 and bottom component 120. The height of the door 500 is configured to fit the distance between the two tracks. In some embodiments, a door knob is included for locking and easy access for the user.

The sliding door 500 is removable from the structure. Components (e.g., all the components) of the structure, including the top component 110 of the portable enclosure 100, the bottom component 120 of the portable enclosure 100, the door 500, the modular toilet seat, shower, waste, and/or other modular components (e.g., modular insert 600) are able to be separated for convenient transportation and storage. A hand washing unit, a dispenser of toilet paper, tissue, or hand sanitizer in the form of a box or cylinder can be affixed to the inner wall or multiple inner walls of the structure in its fully assembled form for use by the occupant.

In the non-affixed instance, when the top component 110 of the portable enclosure 100 is removed from the bottom component 120 of the portable enclosure 100, the top component 110 is able to be turned upside down (so the roof of the structure is now facing towards the ground), and be placed back into the bottom component 120 of the portable enclosure 100 for highly efficient transportation and storage. Because the portable enclosure 100, with all of its modular pieces removed, is reduced to a concave shape (e.g., hollow conical shape, hollow truncated cone, hollow conical frustum, etc.) with walls and a hollow interior, the top component is able to fit into the bottom component. Multiple top components 110 can be stored within other top components 110, or bottom components 120 in other bottom components 120, or bottom components 120 in top components 110, or top components 110 in bottom components 120. There is no inherent limitation in the number of top components 110 and bottom components 120 that can stack together. For example, in one use case, one portable enclosure 100 is taken apart, including a top component 110, a bottom component 120, a door 500, and the modular components (e.g., modular inserts 600), all separated. In another use case, two or more bottom components 120, top components 110, doors 500, and modular components (e.g., modular inserts 600) are transported or stored in conjunction, with the portions of the two portable enclosures 100 stacked into one another in either a stack of four, or a stack of two, or, if there are more units, then a stack of any number without limitation, without discrimination as to whether a top component 110 or bottom component 120 is in a bottom component 120 or top component 110 of the first or second unit, or of any other unit, and with complete interoperability of all modular components, such that the modular components of one unit, as well as the top component and bottom component are interoperable with the bottom component 120 of the other portable enclosure 100. The practical application of this is that users could store and transport a large number of portable toilet enclosures in a relatively small amount of space compared to conventional solutions.

Figure 7C:
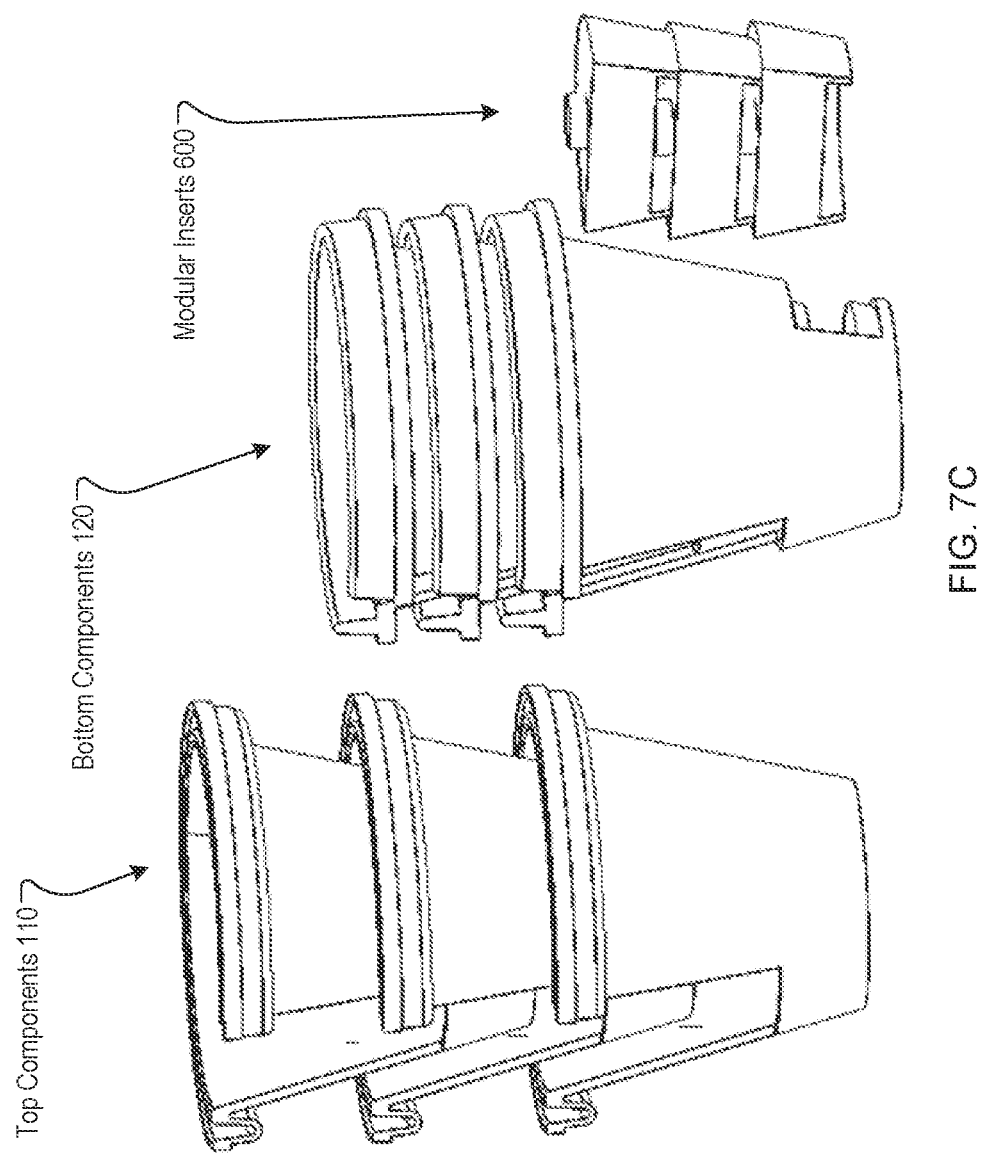

FIGS. 7A-C illustrate perspective views of a portable enclosure 100, according to certain embodiments. FIG. 7A illustrates an assembled perspective view of the portable enclosure 100. FIG. 7B illustrates an exploded perspective view of the portable enclosure 100. FIG. 7C illustrates a stacked perspective view of components of the portable enclosure 100 (e.g., three portable enclosures 100 stacked).

Figure 8:
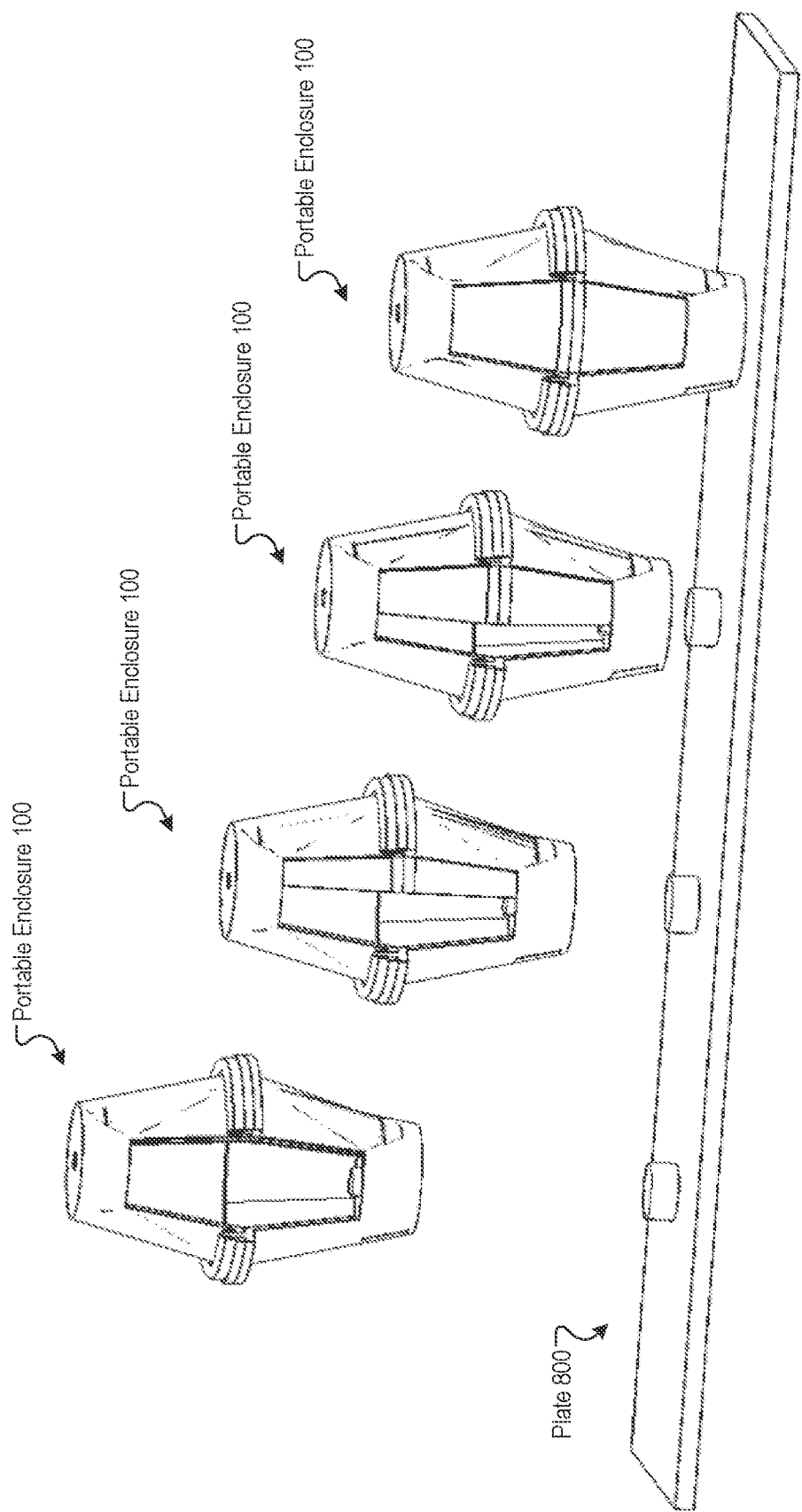
FIG. 8 illustrates a perspective view of a foundation plate and enclosures, according to certain embodiments.

FIG. 8 illustrates a perspective view of a foundation plate 800 and enclosures 100, according to certain embodiments. In some embodiments, the foundation plate 800 hosts one or more portable enclosures 100 (e.g., four portable enclosures 100), secures the portable enclosures 100 in place, and prevents the tipping over of each portable enclosure 100.

In addition to the top component 110 and bottom component 120 of the toilet enclosure herein described, additional components of the present disclosure include a foundation piece, or base-plate, onto which the entire unit with top component 110 and bottom component 120 affixed (e.g., assembled) can connect for stability. This foundation piece or base plate has varying lengths and dimensions; in some embodiments the base plate, which is generally in a range of one half an inch thick up to over one foot thick (measured from the ground), serves to provide stability to one toilet enclosure. In some embodiments the base plate or foundation is longer and has the surface area and attachment spots for multiple portable toilet enclosures to be affixed. The method of affixing the toilet enclosure to the base-plate or foundation is multifarious and includes a click method, a clamp method, a place-and-turn method, a screw method, a rod method, a groove method, or simply placing the unit onto the foundation or into a depression on the top of the foundation where it will achieve varying degrees of structural integrity, but in all cases greater stability and integrity than in the absence of the foundation piece, although the foundation piece is not a necessity for the utilization of the portable toilet enclosure in any of the instances of use described above. As with the other modular components, the base-plate or foundation is as transportable as the rest of the modular components and is interoperable with any unit, whose bottom attachment surface is homogenous. In some embodiments, the base plate or foundation can accommodate a portable toilet enclosure as well as the placement of other modular components such as a handwashing station or shower or changing room or power unit or storage unit onto it, affixing in any of the multiple ways of affixing described above for the portable toilet enclosure.

In some embodiments, the portable enclosure 100 (e.g., portable toilet enclosure) is a rounded shape with a wider middle and with a top and bottom tapering to a smaller cross-section (circular). The top of the portable enclosure 100 (e.g., portable toilet enclosure) has a circular opening or aperture. The opening or aperture can serve to ventilate the portable enclosure 100, allowing a free-flow of air in-and-out of the unit. In some embodiments a small circular piece of plastic fits into the hole, closing it off. In some embodiments the bottom of the unit has a similar hole for drainage, which can be sealed with a cap made of the same or different material as the rest of the structure. In some embodiments additional modular components such as a pipe, antenna, motorized ventilation, or other device can fit into the aperture. In some embodiments the cross-section (from a top-down view) is oval. The top-down cross sections could be circular, square, rectangular, triangular, oval, or another shape, and the dimensions could be constant from top-to-bottom, or else in some embodiments widen-out from the top to the middle and from the bottom to the middle, such that the middle includes the widest portion, or else in some embodiments the unit could widen-out from top-to-bottom, so that the bottom or base where it affixes to the foundation or sits on the ground has the widest profile. In some embodiments, the top component and bottom component have the same weight, and in some embodiments the bottom component is heavier.

In some embodiments, the portable enclosure 100 (e.g., portable toilet enclosure) is rectangular, square, or trapezoidal shaped in cross-section (e.g., a hollow rectangle, a hollow square, a hollow truncated pyramid), with the same general properties as the circular version. In both instances a sliding door or a traditional hinged door can be used. In another instance there is no slider or hinge, but merely a flexible plastic connection between the door and the rest of the unit. In another instance, a window blind design is employed in which a flexible covering is attached to a pulley which allows the user to adjust the level of enclosure by pulling the string attached to the pulley.

The size of the portable enclosure 100 (e.g., unit) may be comparable to existing portable units, colloquially "porta potties," with a height of about 7.5 feet, and a diameter of about 4.5 feet, and can comfortably fit one adult human occupant, although it would be large enough to fit multiple occupants.

The portable enclosure 100 (e.g., portable, modular, toilet and/or multi-purpose enclosure) is configured to be transported and assembled or pieced-together on-site or to arrive on-site already assembled or pieced-together, with the components at a minimum including a top component 110 and a bottom component 120, with additional modular components including a foundation or base-plate, a door 500, a toilet seat and waste tank, a top-hole plug, and dispensers of hand soap, hand sanitizer, toilet paper, and paper towels. The portable enclosure 100 (e.g., unit) is large enough to fit at least one adult human occupant.

The portable enclosure 100 (e.g., portable, modular, toilet and/or multi-purpose enclosure) may be constructed out of one or more materials. In some embodiments, the materials of construction are thermoplastics, which can be manufactured through rotational molding, blow molding, or injection molding. In another, fiberglass is the build material. In another, wood. In another, metal. In another, carbon fiber. In the plastic embodiment, the components include one or more types of plastic, or of one type of plastic, and have one or multiple colors, and one or multiple finishes, including a finish designed to protect the plastic from tampering, including from carving and graffiti. In some embodiments, the portable enclosure 100 is to be constructed using one or more manufacturing techniques including roto-molding, hand-crafted, mold-poured, or sheeting, in which case the sheeting can be connected using heat, or hardware such as, but not limited to, fasteners, clamps, and screws.

FIGS. 9A-D illustrate components of portable enclosures 100, according to certain embodiments. FIG. 9A illustrates a bottom component 120. FIG. 9B illustrates a top component 110 and a bottom component 120 (e.g., fastened together). FIG. 9C illustrates a vent insert 900, a modular insert 600, and a door 500. FIG. 9D illustrates a vent insert 900, a modular insert 600, and a door 500 coupled to the top component 110 and/or bottom component 120 (e.g., that are fastened together.

Figures 10A, 10B:
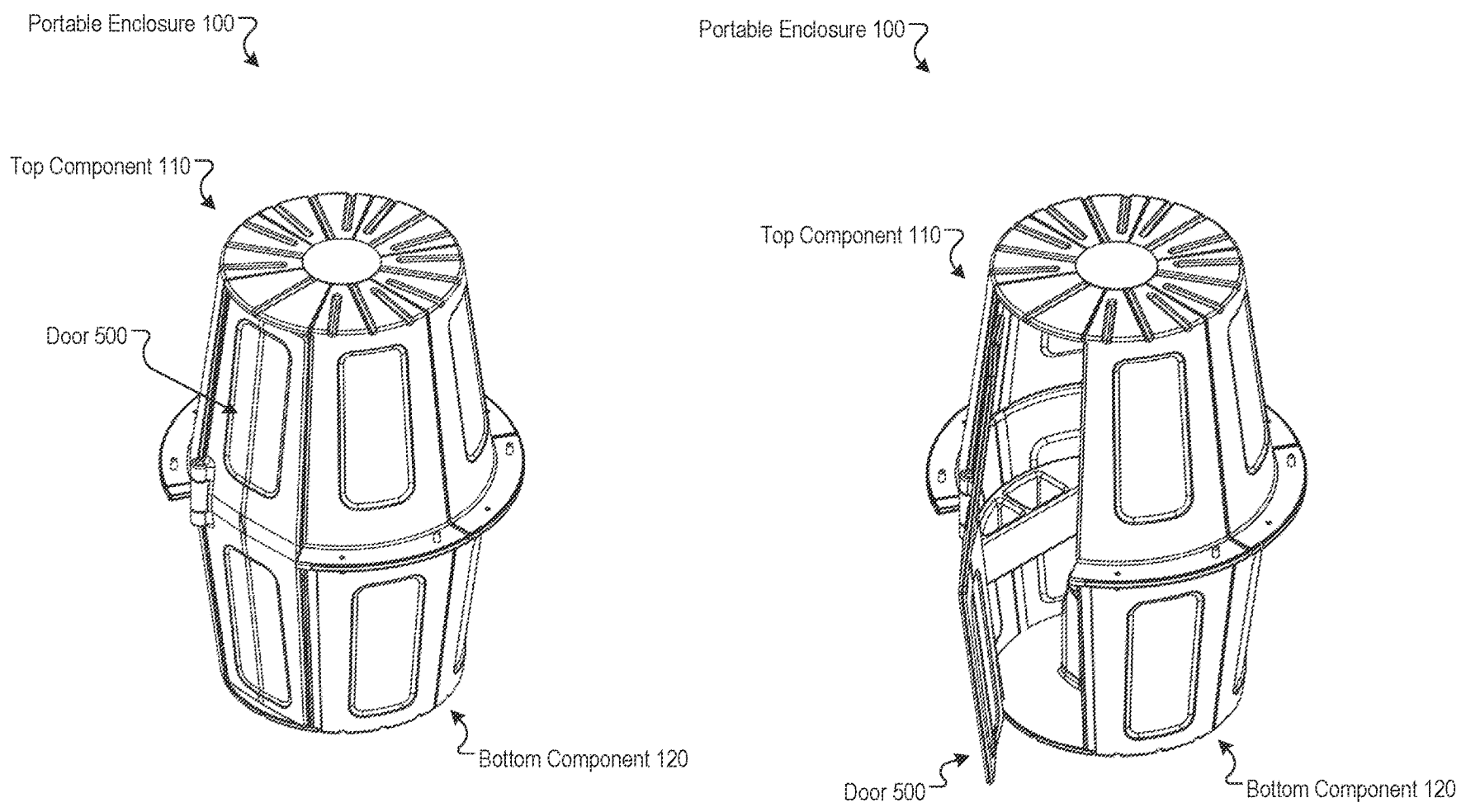

FIGS. 10A-D illustrate views of portable enclosures 100, according to certain embodiments. FIG. 10A illustrates a swinging door that is in a closed position. FIG. 10B illustrates a swinging door that is in an open position. FIGS. 10C-D illustrate exploded views of portable enclosures 100.

Figures 11A, 11B:
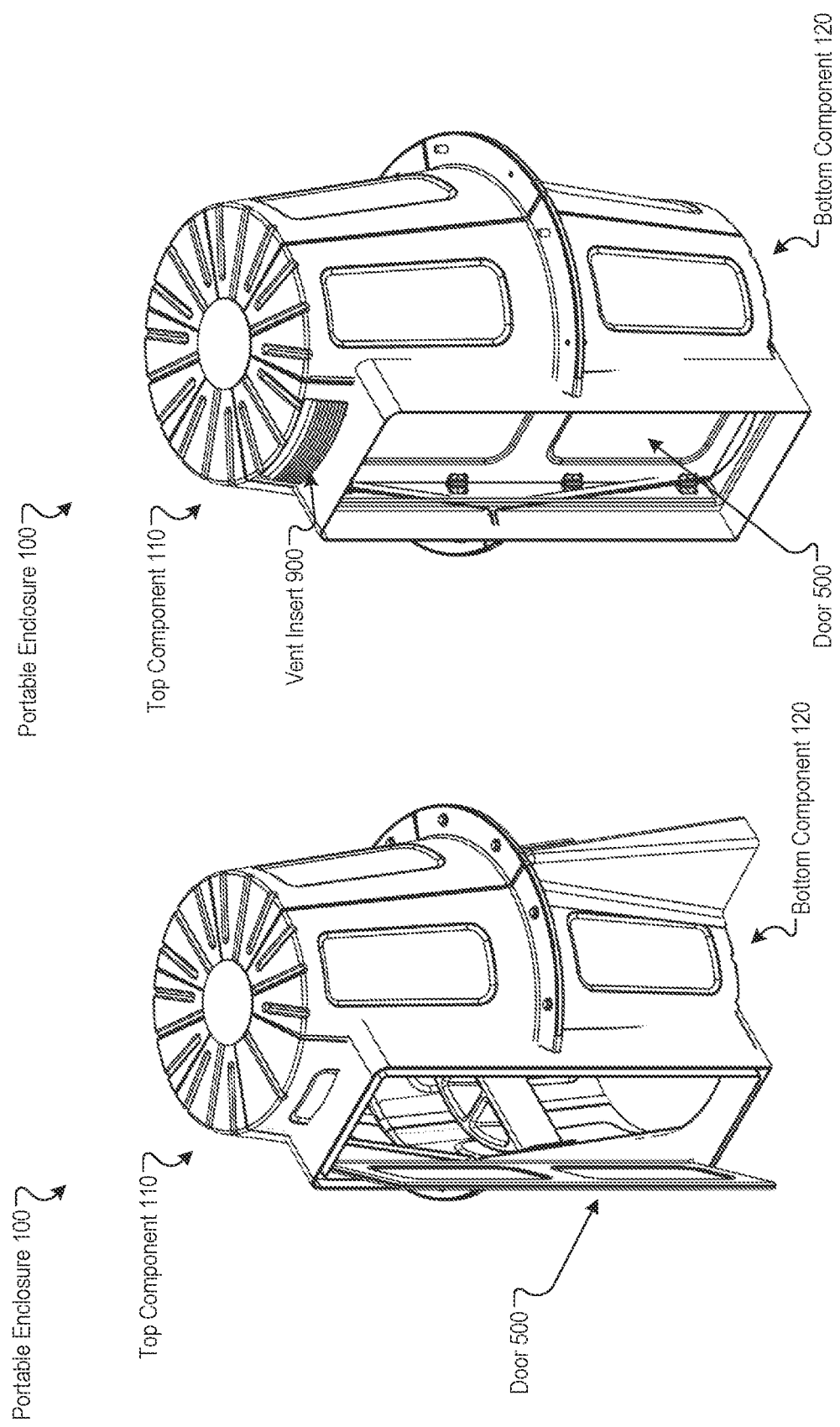

FIGS. 11A-D illustrate views of portable enclosures 100, according to certain embodiments. FIG. 11A illustrates a swinging door that is in an open position. FIG. 11B illustrates a swinging door that is in a closed position. FIGS. 11C-D illustrate exploded views of portable enclosures 100.

Figures 12A, 12B, 12C:
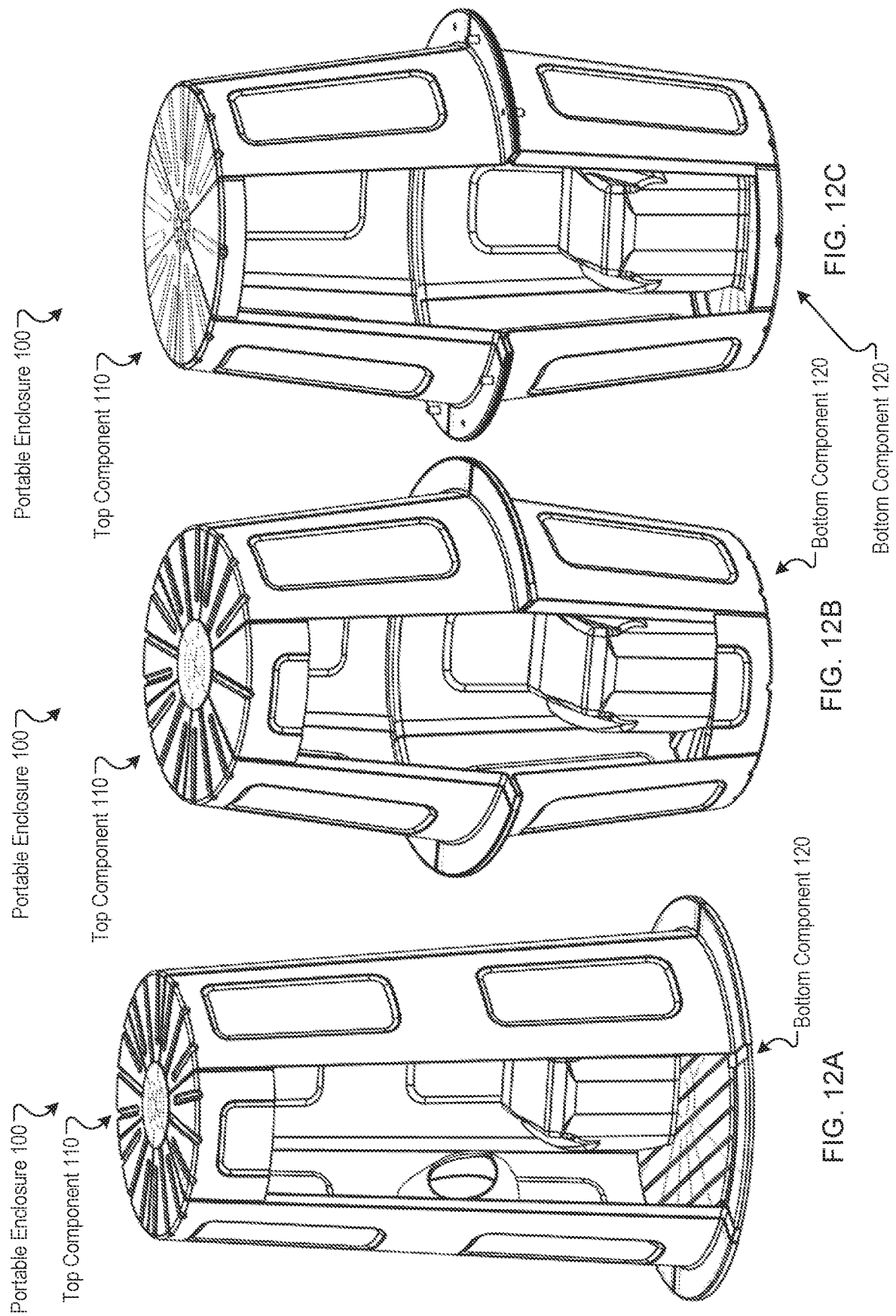
FIGS. 12A-C illustrate views of portable enclosures, according to certain embodiments.

FIGS. 12A-C illustrate views of portable enclosures 100, according to certain embodiments.

Figure 13A:
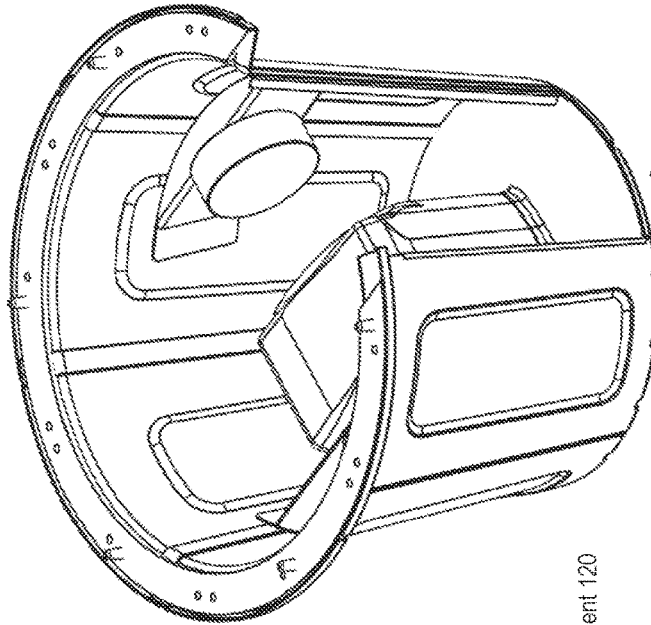
FIGS. 13A-D illustrate components of portable enclosures, according to certain embodiments.
Figure 13B:
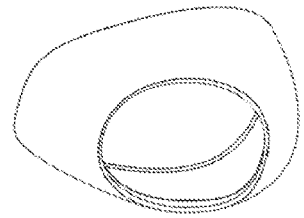
Figure 13C:
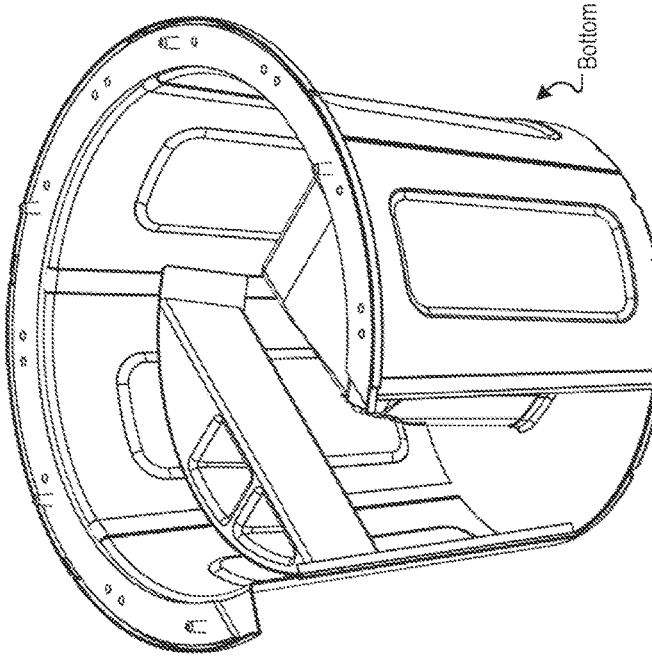
Figure 13D:
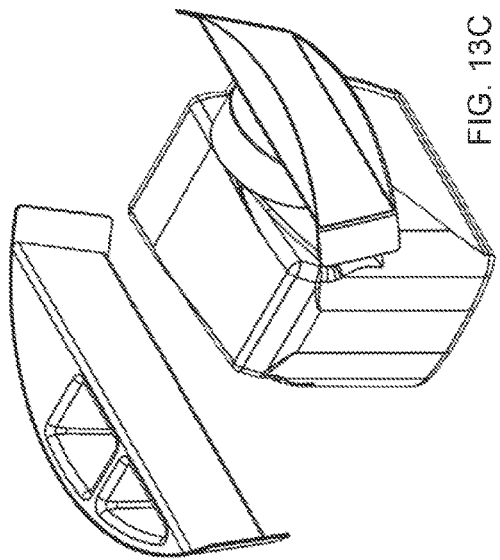
Figure 14A:
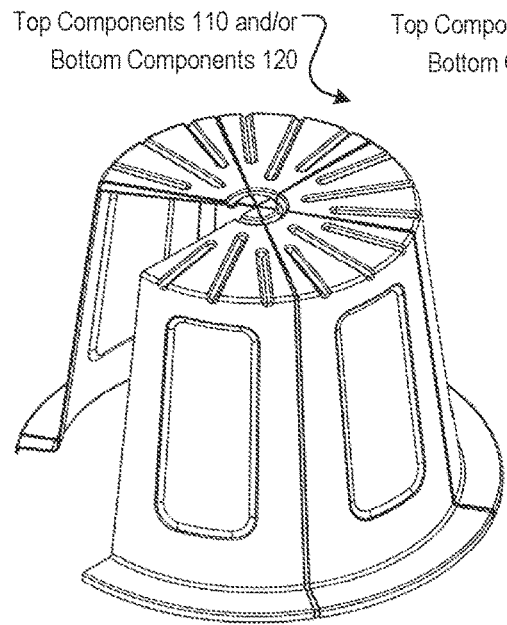
FIGS. 14A-H illustrate components of portable enclosures, according to certain embodiments.
Figure 14B:
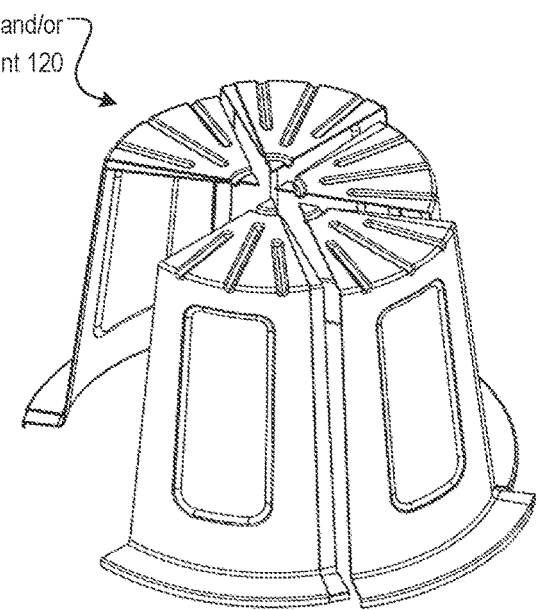
Figure 14C:
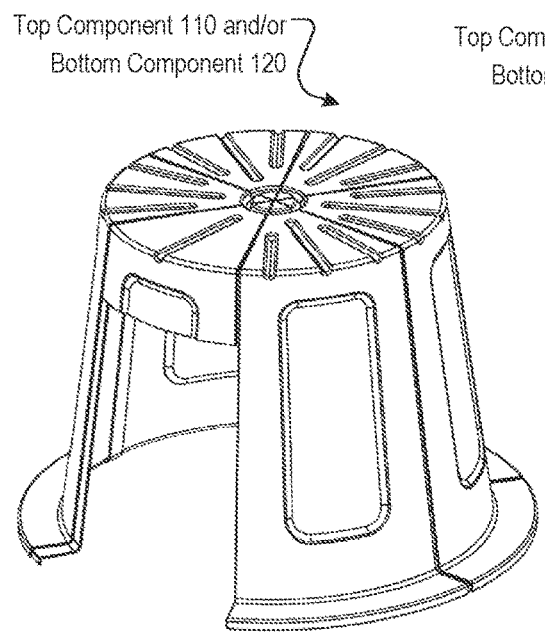
Figure 14D:
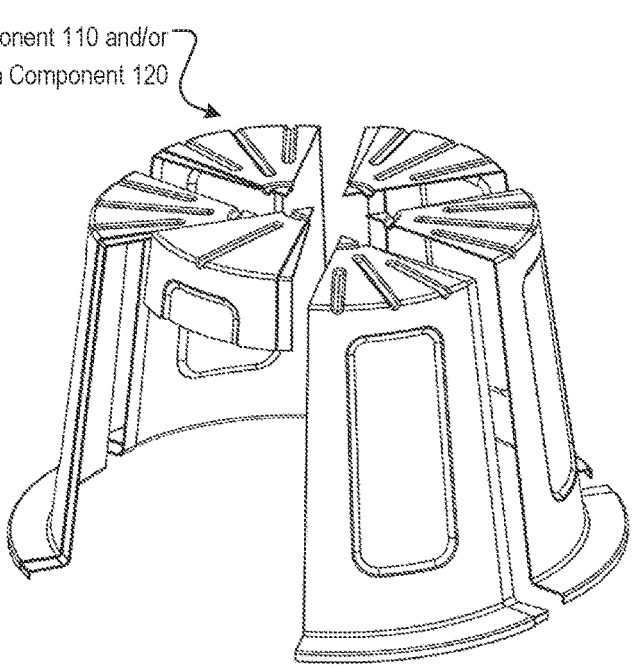
Figure 14E:
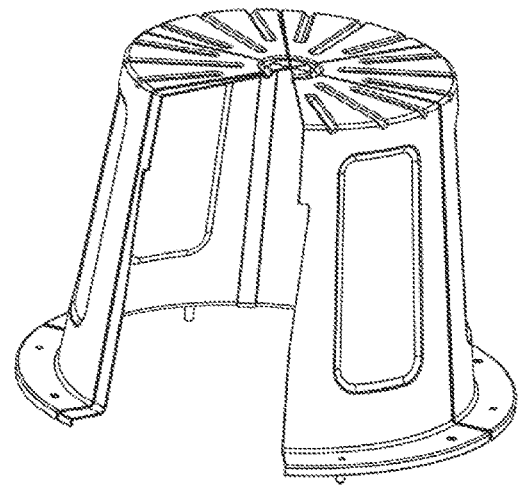
Figure 14F:
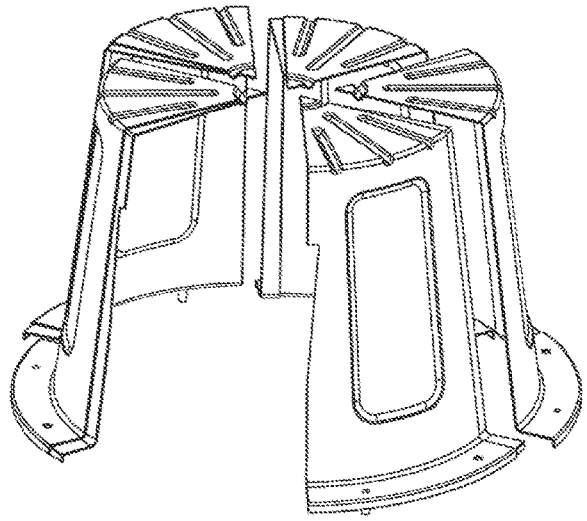
Figure 14G:
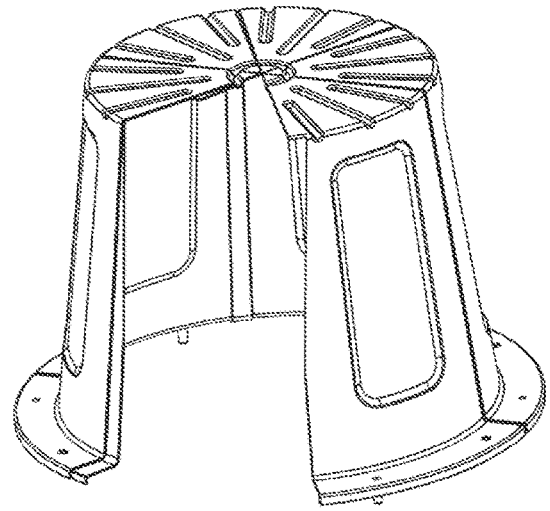
Figure 14H:
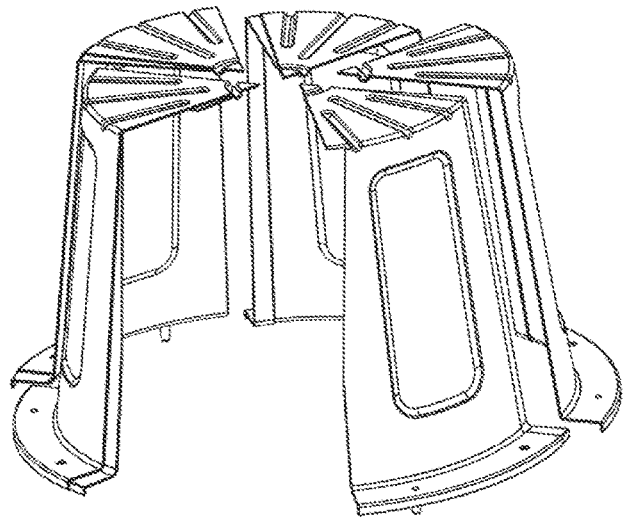

FIGS. 13A-D illustrate components of portable enclosures 100, according to certain embodiments. FIG. 13A illustrates components (e.g., toilet, sink, etc.) coupled to a bottom component 120. FIG. 13B illustrates components (e.g., toilet, toilet paper dispenser, etc.) coupled to a bottom component 120. FIG. 13C illustrates components (e.g., toilet, sink, toilet paper dispenser, etc.) to be coupled to a bottom component 120. FIG. 13D illustrates a component (e.g., urinal) to be coupled to a bottom component 120.

FIGS. 14A-H illustrate components of portable enclosures 100, according to certain embodiments. FIGS. 14A, 14C, 14E, and 14G illustrate an assembled view of top component 110 and/or bottom component 120. FIGS. 14B, 14D, 14F, and 14H illustrate an exploded view of top component 110 and/or bottom component 120.

FIGS. 15A-B illustrate stacked components of portable enclosures 100, according to certain embodiments. FIG. 15A illustrates a cross-section of one or more top components 110 and/or one or more bottom components 120. FIG. 15B illustrates a perspective view of one or more top components 110 and/or one or more bottom components 120.

In some embodiments, the top structure 110 and/or bottom structure are in a panelized construction (e.g., adhering to PSAAI guidelines that govern portable sanitation so that the portable enclosures 100 are compliant) and so that final delivery of the portable disclosure is stable, safe, and sustainable design for mass production transition.

In some embodiments, the mid-joint (e.g., where the top component 110 couples to the bottom component 120) includes a locking mechanism (e.g., or line-up of top and bottom holes to fit a padlock through) that allows the assembly of a portable enclosure 100 to take under about 30 seconds and to provide tamper-proof interlocks that are only accessible by special keys.

In some embodiments, the door 500 is a sliding door or a hinge door while maintaining the ability to stack units.

In some embodiments, the toilet/tank system is off-the shelf toilet/tank system. In some embodiments, the toilet of the portable enclosure 100 is a self-contained flushing toilet system (e.g., about 23 inches wide, about 24.5 inches deep, 15 gallon capacity, seat is about 21.5" high, only moving parts are flapper valve and tough rubber-sealed foot pump). The toilet may be secured to the bottom component 120 in the assembled configuration and may be removed from the bottom component 120 for transportation.

The portable enclosure 100 may include a toilet paper holder, a door-lock mechanism (e.g., with occupancy indicator), a ultra violet (UV) light (e.g., for hygiene), and/or a fan in the ceiling.

The door 500 may be a sliding door, a swinging door, a revolving door, or another type of door.

The mainframe and entire unit may be single-bodied or panelized version (e.g., pizza slices). With the panels (e.g., pizza slices), the ease of manufacturing is increased since the pieces are put together to form a whole unit, rather than manufacturing one large piece of plastic.

In the above description, numerous details are set forth. It will be apparent, however, to one of ordinary skill in the art having the benefit of this disclosure, that embodiments may be practiced without these specific details. In some instances, well-known structures and devices are shown in block diagram form, rather than in detail, in order to avoid obscuring the description.

The terms "over," "under," "between," "disposed on," and "on" as used herein refer to a relative position of one material layer or component with respect to other layers or components. For example, one layer disposed on, over, or under another layer may be directly in contact with the other layer or may have one or more intervening layers. Moreover, one layer disposed between two layers may be directly in contact with the two layers or may have one or more intervening layers. Similarly, unless explicitly stated otherwise, one feature disposed between two features may be in direct contact with the adjacent features or may have one or more intervening layers.

Various embodiments can have different combinations of the structural features described above. For instance, all optional features of an enclosure described above can also be implemented in an enclosure and specifics in the examples can be used anywhere in one or more embodiments.

While the present disclosure has been described with respect to a limited number of embodiments, those skilled in the art will appreciate numerous modifications and variations therefrom. It is intended that the appended claims cover all such modifications and variations as fall within the true spirit and scope of this present disclosure.

In the description herein, numerous specific details are set forth, such as examples of specific types of material, specific sizes, specific surfaces, specific structures, specific details, specific configurations, specific types, specific system components, etc. in order to provide a thorough understanding of the present disclosure. It will be apparent, however, to one skilled in the art that these specific details need not be employed to practice the present disclosure. In other instances, well known components or methods, such as specific and alternative material, sizes, surfaces, structures, details, configurations, types, system components, etc. have not been described in detail in order to avoid unnecessarily obscuring the present disclosure. In some embodiments, one or more of the dimensions described herein may be varied by +/−1%. In some embodiments, one or more of the dimensions described herein may be varied by +/−5%. In some embodiments, one or more of the dimensions described herein may be varied by +/−10%. In some embodiments, one or more of the dimensions described herein may be varied by +/−15%. In some embodiments, one or more of the dimensions described herein may be varied by +/−20%. In some embodiments, one or more of the dimensions described herein may not be used.

Although some of the embodiments herein are described with reference to a portable toilet enclosure, other embodiments are applicable to other types of enclosures. Although some of the embodiments herein are described with reference to a portable enclosure forming a toilet room, other embodiments are applicable, such as portable enclosures forming a shower room, a changing room, or the like. In some embodiments, the portable enclosure has multiple uses (e.g., can be used as two or more of a toilet room, shower room, changing room, and/or the like). Similar techniques and teachings of embodiments of the present disclosure can be applied to other types of components, devices, systems, and assemblies. In addition, the description herein provides examples, and the accompanying drawings show various examples for the purposes of illustration. However, these examples should not be construed in a limiting sense as they are merely intended to provide examples of embodiments of the present disclosure rather than to provide an exhaustive list of all possible implementations of embodiments of the present disclosure.

Use of the phrase 'configured to,' in one embodiment, refers to arranging, putting together, manufacturing, offering to sell, importing and/or designing an apparatus, hardware, or element to perform a designated or determined task. In this example, an apparatus or element thereof that is not operating is still 'configured to' perform a designated task if it is designed, coupled, and/or interconnected to perform said designated task.

Furthermore, use of the phrases 'to,' 'capable of/to,' and or 'operable to,' in one embodiment, refers to some apparatus, hardware, and/or element designed in such a way to enable use of the apparatus, hardware, and/or element in a specified manner. Note that use of to, capable to, or operable to, in one embodiment, refers to the latent state of an apparatus, hardware, and/or element, where the apparatus, hardware, and/or element is not operating but is designed in such a manner to enable use of an apparatus in a specified manner.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

In the foregoing specification, a detailed description has been given with reference to specific exemplary embodiments. It will, however, be evident that various modifications and changes can be made thereto without departing from the broader spirit and scope of the disclosure as set forth in the appended claims. The specification and drawings are, accordingly, to be regarded in an illustrative sense rather than a restrictive sense. Furthermore, the foregoing use of embodiment and other exemplarily language does not necessarily refer to the same embodiment or the same example, but can refer to different and distinct embodiments, as well as potentially the same embodiment.

The words "example" or "exemplary" are used herein to mean serving as an example, instance or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Also, the terms "first," "second," "third," "fourth," etc. as used herein are meant as labels to distinguish among different elements and can not necessarily have an ordinal meaning according to their numerical designation.

The above description of illustrated implementations of the disclosure, including what is described in the Abstract, is not intended to be exhaustive or to limit the disclosure to the precise forms disclosed. While specific implementations of, and examples for, the disclosure are described herein for illustrative purposes, various equivalent modifications are possible within the scope of the disclosure, as those skilled in the relevant art will recognize.

What is claimed is:

1. A portable enclosure comprising:
    a bottom component comprising:
        a first sidewall that forms a first door opening; and
        a first flange that extends from an upper portion of the first sidewall;
    a top component comprising:
        a second sidewall that forms a second door opening; and
        a second flange that extends from a lower portion of the second sidewall,
    wherein the top component is configured to removably attach to the bottom component via a junction between a protrusion and a recess to align the first door opening and the second door opening and to at least partially enclose an interior volume of the portable enclosure, at least one of the protrusion or the recess being offset from at least one of the first sidewall or the second sidewall; and
    a door configured to removably attach to the top component and the bottom component to cover the first door opening and the second door opening, wherein:
        the first flange forms the protrusion of the junction and the second flange forms the recess of the junction; or
        the second flange forms the protrusion of the junction and the first flange forms the recess of the junction.

2. The portable enclosure of claim 1, wherein the bottom component is a first hollow conical frustum and the top component is a second hollow conical frustum, and wherein the bottom component is stackable with at least one of one or more other bottom components or the top component.

3. The portable enclosure of claim 1, wherein the portable enclosure is one or more of a portable toilet structure, a portable shower structure, or a portable changing room structure.

4. The portable enclosure of claim 1, wherein the bottom component has substantially same dimensions as the top component, the bottom component and the top component being substantially equal halves of the portable enclosure.

5. The portable enclosure of claim 1, wherein the first sidewall and the second sidewall do not overlap responsive to the top component and the bottom component being in an assembled configuration, and wherein the first sidewall and the second sidewall overlap responsive to the top component and the bottom component being in a stacked configuration.

6. The portable enclosure of claim 1, wherein the second sidewall is disposed on the first sidewall without overlapping the first sidewall responsive to the top component and the bottom component being in an assembled configuration.

7. The portable enclosure of claim 1, wherein:
    the bottom component comprises a bottom wall at a first distal end of the bottom component, the bottom wall being configured to be disposed on a substantially horizontal surface;
    the bottom component is configured to attach to the top component at a second distal end of the bottom component via the junction between the protrusion and the recess that are laterally offset from the first sidewall and the second sidewall; and the interior volume has a first width proximate the first distal end of the bottom component that is smaller than a second width of the interior volume proximate the second distal end of the bottom component.

8. The portable enclosure of claim 7, wherein:

the top component comprises a top wall at a first distal end of the top component;

the top component is configured to attach to the bottom component at a second distal end of the top component via the junction between the protrusion and the recess that are laterally offset from the first sidewall and the second sidewall; and the interior volume has the first width proximate the first distal end of the top component and the second width proximate the second distal end of the top component.

9. The portable enclosure of claim 7, wherein a connection plane of the bottom component and the top component is between the first sidewall and the second sidewall without overlapping the first sidewall and without overlapping the second sidewall.

10. The portable enclosure of claim 1, wherein the first sidewall has a substantially circular first perimeter, and wherein the second sidewall has a substantially circular second perimeter.

11. The portable enclosure of claim 7 further comprising one or more of a toilet coupled to the bottom wall of the bottom component in the interior volume or a urinal coupled to the first sidewall of the bottom component in the interior volume.

12. The portable enclosure of claim 1 further comprising a toilet paper holder coupled to the first sidewall of the bottom component in the interior volume.

13. The portable enclosure of claim 1 further comprising a door lock configured to indicate occupancy responsive to the door being in a locked configuration.

14. The portable enclosure of claim 1 further comprising an ultra violet light disposed in the interior volume and configured to sanitize one or more surfaces in the interior volume.

15. The portable enclosure of claim 1 further comprising a fan configured to flow air through the interior volume.

16. A portable enclosure comprising:

a plurality of panels comprising:

a first subset of the plurality of panels forming a top component, wherein the top component comprises:

a first sidewall that forms a first door opening; and a first flange that extends from an upper portion first sidewall;

a second subset of the plurality of panels forming a bottom component, wherein the bottom component comprises:

a second sidewall that forms a second door opening; and a second flange that extends from a lower portion of the second sidewall, wherein the top component couples to the bottom component via a junction between a protrusion and a recess to form an interior volume of the portable enclosure and to align the first door opening and the second door opening, at least one of the protrusion or the recess being offset from at least one of the first sidewall or the second sidewall, wherein each panel of the plurality of panels comprises:

a top wall that is substantially horizontal; and a bottom wall that is substantially horizontal and is configured to be coupled to corresponding bottom wall of a second panel; and a corresponding sidewall that is disposed between the top wall and the bottom wall, wherein:

the first flange forms the protrusion of the junction and the second flange forms the recess of the junction; or the second flange forms the protrusion of the junction and the first flange forms the recess of the junction.

17. The portable enclosure of claim 16, wherein the corresponding sidewall is angled to form an angle between a bottom surface of the top wall and an interior surface of the corresponding sidewall that is greater than ninety degrees.

18. The portable enclosure of claim 16, wherein each panel of the plurality of panels further comprises:

a front flange extending along the top wall, the corresponding sidewall, and the bottom wall; and a rear feature extending along the top wall, the corresponding sidewall, and the bottom wall, wherein the rear feature is opposite the front flange, wherein the front flange is configured to couple to a corresponding rear feature of a third panel, wherein the rear feature is configured to couple to a corresponding front flange of a fourth panel.

19. A method comprising:

coupling a top component of a portable enclosure to a bottom component of the portable enclosure via a junction between a protrusion and a recess to align a first door opening formed by the top component with a second door opening formed by the bottom component and to form an interior volume of the portable enclosure, the bottom component comprising a first sidewall that forms the first door opening and a first flange that extends from an upper portion of the first sidewall, the top component comprising a second sidewall that forms the second door opening and a second flange that extends from a lower portion of the second sidewall, at least one of the protrusion or the recess being offset from at least one of the first sidewall or the second sidewall, wherein:

the first flange forms the protrusion of the junction and the second flange forms the recess of the junction; or the second flange forms the protrusion of the junction and the first flange forms the recess of the junction;

coupling a door to the top component via the first door opening and to the bottom component via the second door opening; and installing one or more components in the interior volume.

20. The method of claim 19, wherein the one or more components comprise one or more of a toilet, a urinal, a toilet paper holder, an ultra violet light, or a fan.

* * * * *